United States Patent
Bippart et al.

(10) Patent No.: US 10,441,259 B2
(45) Date of Patent: Oct. 15, 2019

(54) WOUND CLOSURE APPARATUS AND METHOD

(71) Applicant: Surgical Innovations LLC, Marysville, NJ (US)

(72) Inventors: Peter E. Bippart, Oroville, CA (US); Diane S. Kindred, Yuba City, CA (US)

(73) Assignee: Surgical Innovations LLC, Marysville, CA (US)

( * ) Notice: Subject to any disclaimer, the term of this patent is extended or adjusted under 35 U.S.C. 154(b) by 0 days.

(21) Appl. No.: 16/286,507

(22) Filed: Feb. 26, 2019

(65) Prior Publication Data

US 2019/0231327 A1 Aug. 1, 2019

Related U.S. Application Data

(60) Continuation-in-part of application No. 16/275,222, filed on Feb. 13, 2019, which is a continuation-in-part
(Continued)

(51) Int. Cl.
*A61B 17/00* (2006.01)
*A61B 90/00* (2016.01)
*A61B 1/07* (2006.01)

(52) U.S. Cl.
CPC ............ *A61B 17/0057* (2013.01); *A61B 1/07* (2013.01); *A61B 2017/00004* (2013.01);
(Continued)

(58) Field of Classification Search
CPC ...... A61B 17/0057; A61B 2017/00004; A61B 2017/00526; A61B 2017/00871;
(Continued)

(56) References Cited

U.S. PATENT DOCUMENTS

| | | |
|---|---|---|
| 2,324,520 A | 7/1943 | Lamson |
| 3,447,533 A | 6/1969 | Spicer |

(Continued)

FOREIGN PATENT DOCUMENTS

| | | |
|---|---|---|
| WO | WO-2004/024030 A1 | 3/2004 |
| WO | WO-2005/011352 A2 | 2/2005 |

OTHER PUBLICATIONS

Anonymous. (Aug. 2, 2013). "Increasing Demand for Minimally Invasive Surgeries Drives Growth in the Endoscopy Systems Market, According to New Report by Global Industry Analysts, Inc." Endoscopy Systems: A Global Strategic Business Report. Global Industry Analysts, Inc. San Jose, CA. (PRWEB) Web www.prweb.com, two pages, date viewed: Feb. 14, 2014.
(Continued)

*Primary Examiner* — Phong Son H Dang
(74) *Attorney, Agent, or Firm* — Morrison and Foerster LLP

(57) ABSTRACT

A wound closure apparatus can be a self-contained device for delivery and deployment of a wound plug. The apparatus can include a post having a first end and a second end, wherein the first end of the post includes a coupling attachment. The apparatus can include a rod having a first end, a second end and a rod cavity that extends from the first end of the rod to the second end of the rod. The apparatus can also include a wound plug, having a first end, a second end, and a breakaway connection located between the first end and second end of the wound plug. In in an assembled configuration, the post can extend through the rod cavity and be detachably coupled to the breakaway connection such that the first end of the wound plug is positioned adjacent the second end of the rod.

14 Claims, 20 Drawing Sheets

Related U.S. Application Data of application No. 15/449,818, filed on Mar. 3, 2017, now Pat. No. 10,219,797, which is a division of application No. 14/634,421, filed on Feb. 27, 2015, now Pat. No. 9,615,817.

(52) U.S. Cl.
CPC ........... A61B 2017/00115 (2013.01); A61B 2017/00407 (2013.01); A61B 2017/00526 (2013.01); A61B 2017/00606 (2013.01); A61B 2017/00623 (2013.01); A61B 2017/00637 (2013.01); A61B 2017/00871 (2013.01); A61B 2017/00884 (2013.01); A61B 2017/00889 (2013.01); A61B 2090/037 (2016.02)

(58) Field of Classification Search
CPC .... A61B 2090/037; A61B 2017/00115; A61B 2017/00606; A61B 2017/00884; A61B 2017/00623
See application file for complete search history.

(56) References Cited

U.S. PATENT DOCUMENTS

| | | | |
|---|---|---|---|
| 4,007,743 A * | 2/1977 | Blake | A61B 17/0057 606/232 |
| 4,532,926 A * | 8/1985 | O'Holla | A61B 17/0643 606/220 |
| 4,935,028 A | 6/1990 | Drews | |
| 5,192,301 A | 3/1993 | Kamiya et al. | |
| 5,342,393 A * | 8/1994 | Stack | A61B 17/0057 24/453 |
| 5,350,399 A * | 9/1994 | Erlebacher | A61B 17/0057 128/899 |
| 5,366,460 A | 11/1994 | Eberbach | |
| RE34,886 E | 2/1995 | Kensey et al. | |
| 5,620,461 A | 4/1997 | Muijs Van De Moer et al. | |
| 5,725,552 A * | 3/1998 | Kotula | A61B 17/0057 604/285 |
| 5,853,422 A | 12/1998 | Huebsch et al. | |
| 5,879,366 A | 3/1999 | Shaw et al. | |
| 6,120,539 A | 9/2000 | Eldridge et al. | |
| 6,241,768 B1 | 6/2001 | Agarwal et al. | |
| 7,798,953 B1 * | 9/2010 | Wilk | A61B 17/0057 600/16 |
| 8,398,676 B2 * | 3/2013 | Roorda | A61B 17/0057 606/213 |
| 8,506,593 B2 | 8/2013 | Klein et al. | |
| 8,657,852 B2 * | 2/2014 | Roorda | A61B 17/0057 606/213 |
| 8,992,567 B1 * | 3/2015 | Houser | A61B 17/08 606/213 |
| 9,089,311 B2 * | 7/2015 | Fortson | A61B 17/0057 |
| 9,241,696 B2 * | 1/2016 | Mehl | A61B 17/0057 |
| 9,295,456 B2 * | 3/2016 | Subramanian | A61B 17/0057 |
| 9,615,817 B2 | 4/2017 | Bippart et al. | |
| 10,219,797 B2 | 3/2019 | Bippart et al. | |
| 2002/0042622 A1 * | 4/2002 | Vargas | A61B 17/11 606/153 |
| 2005/0273135 A1 * | 12/2005 | Chanduszko | A61B 17/0057 606/213 |
| 2006/0015142 A1 * | 1/2006 | Malazgirt | A61B 17/0057 606/213 |
| 2006/0190036 A1 * | 8/2006 | Wendel | A61B 17/0057 606/213 |
| 2006/0206146 A1 * | 9/2006 | Tenerz | A61B 17/0057 606/213 |
| 2007/0073337 A1 * | 3/2007 | Abbott | A61B 17/0057 606/213 |
| 2007/0123817 A1 | 5/2007 | Khosravi et al. | |
| 2007/0179527 A1 * | 8/2007 | Eskuri | A61B 17/0057 606/213 |
| 2007/0185529 A1 * | 8/2007 | Coleman | A61B 17/0057 606/213 |
| 2007/0276415 A1 * | 11/2007 | Kladakis | A61B 17/0057 606/151 |
| 2008/0208226 A1 * | 8/2008 | Seibold | A61B 17/0057 606/158 |
| 2008/0215089 A1 | 9/2008 | Williams et al. | |
| 2009/0088795 A1 * | 4/2009 | Cahill | A61B 17/0057 606/215 |
| 2009/0312789 A1 * | 12/2009 | Kassab | A61B 17/0057 606/213 |
| 2010/0016885 A1 | 1/2010 | Eidenschink et al. | |
| 2010/0114156 A1 * | 5/2010 | Mehl | A61B 17/0057 606/213 |
| 2010/0114159 A1 * | 5/2010 | Roorda | A61B 17/0057 606/215 |
| 2010/0179590 A1 * | 7/2010 | Fortson | A61B 17/0057 606/216 |
| 2011/0077683 A1 * | 3/2011 | Huss | A61B 17/0057 606/213 |
| 2011/0082495 A1 * | 4/2011 | Ruiz | A61B 17/0057 606/213 |
| 2011/0184439 A1 * | 7/2011 | Anderson | A61B 17/0057 606/151 |
| 2012/0078295 A1 * | 3/2012 | Steiner | A61B 17/0057 606/213 |
| 2013/0012987 A1 * | 1/2013 | Klein | A61B 17/0057 606/213 |
| 2013/0165963 A1 * | 6/2013 | Coleman | A61B 17/1204 606/192 |
| 2014/0200597 A1 | 7/2014 | Klein et al. | |

OTHER PUBLICATIONS

Cell. Incorporated, Matristem®, Acell Inc., located at: www.ACell.com, two pages.

Chinese Search Report dated Aug. 10, 2018, for CN Patent Application 201580079181.4, four pages with English translation.

Connekt, LLC. (Dec. 11, 2017). "A Revolutionary Patented Surgical Apparatus Designed by Connekt, LLC," YouTube, located at: https://www.youtube.com/watch?v=deZLLd818Gk&feature=youtu.be, last visited on Feb. 13, 2019, one page.

Delancey, J. O. M.D., et al. "Operations on the Abdominal Wall." Glob.libr.women's med., (ISSN:1756-2228) 2008; Web. www.glowm.com (DOI 10.3843/GLOWM.10038), 20 pages, date viewed: Oct. 12, 2013.

Dhandayuthapani, B., et al. (Jul. 9, 2011)."Polymeric Scaffolds in Tissue Engineering Application: A Review," International Journal of Polymer Science: vol. 2011, Article ID 290602, Hindawi Publishing Corp. Web (Locate by DOI No. 10.1155/2011/290602), 20 pages, date viewed: Feb. 14, 2014.

Extended European Search Report dated Oct. 25, 2018, for EP Application No. 15883638.7, six pages.

Gamal EM, et al., (1997). "Late Epigastric Incisional Hernias following Laparoscopic Cholecystectomy." Acta Chir Hung. 36 (1-4) 1997. pp. 95-96. PubMed-NCBI US National Library of Medicine National Institutes of Health (NCBI) Web www.PubMed.gov <http://www.PubMed.gov> two pages, date viewed: Mar. 10, 2014.

Hamood, A. M., et al. (Sep.-Dec. 2009). "Different Port Closure Techniques in Laparoscopy Surgery," World Journal of Laparoscopic Surgery, vol. 2 (3), p. 29-38; (Total 60 pages) International Scientific Journals from Jaypee (Jaypee Brothers Medical Publishers (P) Ltd. Web www.jaypeejournals.com (DOI No. for PDF is DOI 10.5005/jp-journals-10007-1003), ten pages, date viewed: date Feb. 13, 2014.

Horst, M., et al. "A Bilayered Hybrid MicroFibrous PLGA-Acellular Matrix Scaffold for Hollow Organ Tissue Engineering," Biomaterials, 34 (5). 2013. Pages 1537-1545. Posted at the Zurich Open Repository and Archive, Un. Of Zurich Web www.ScienceDirect.com (DOI 10.5167/uzh-70363), 21 pages, date viewed: Mar. 13, 2014.

(56) References Cited

OTHER PUBLICATIONS

Hussain, A. et al. (Jul.-Sep. 2009 ). "Long Term Study of Port-Site Incisional Hernia after Laparoscopic Procedures," Journal of the Society of Laparoendoscopic Surgeons 13 (3), pp. 346-349, the Publisher Society of Laparoendoscopic Surgeons, Inc., PMC-US National Library of Medicine National Institutes of Health, Web www.PubMed.gov. <http://www.PubMed.gov>, five pages, date viewed Mar. 1, 2014.
Hutmacher, D. et al, (2000). "Scaffolds in Tissue Engineering Bone and Cartilage," Laboratory for Biomedical Engineering, Institute of Engineering Science, Department of Orthopedic Surgery, National University of Singapore, Singapore, Elsevier Science Ltd, 2529-2543, Web <http://158.110.32.35/download/CURCIO/Hurtmacher-BIO-2000.pdf>, 15 pages, date viewed: Nov. 2013.
International Search Report dated May 13, 2016, for PCT application No. PCT/US2015/067489, five pages. (1.40).
Lawrence, B.J. (Jul. 2006). "Composite Scaffolds of Natural and Synthetic Polymers for Bladder Tissue Engineering," Documentation submitted to the Faculty of the Graduate College of the Oklahoma State Un. for the Degree of Master of Science, , Stillwater, Ok. Web www.digital.library.okstate.ed <http://www.digital.library.okstate.ed>, 63 pages, date viewed: Mar. 3, 2014.
Nezhat, C.H. et al. (Mar. 3, 2011). "Adhesions Prevention and Management," Prevention and Management of Laparoendoscopic Surgical Complications: Society of Laparoendoscopic Surgeons-Focus Clarity Innovation. 3rd Edition, Web: www.laparoscopy.blogs.com <http://www.laparoscopy.blogs.com>, 16 pages, date viewed: Nov. 12, 2013.
Notice of Allowance dated Feb. 22, 2017, for U.S. Appl. No. 14/634,421, filed Feb. 27, 2015, ten pages.
Notice of Allowance dated Oct. 23, 2018, for U.S. Appl. No. 15/449,818, filed Mar. 3, 2017, eight pages.
Notice of Allowance (corrected) dated Dec. 5, 2018, for U.S. Appl. No. 15/449,818, filed Mar. 3, 2017, four pages.
Petro, C. et al. (2010). "Repair of Ventral Abdominal Wall Hernias," Chapter 27, Gastrointestinal Tract and Abdomen—Section 05, ACS Surgery: Principles and Practice, Decker Intellectual Properties Inc., Scientific American Surgery, <http://www.sciamsurgery.com/sciamsurgery/institutional/regGetFile.action?fileName=part05_ch21.pdf>, 30 pages, date viewed: Feb. 20, 2014.
Seamon, L.G., et al. (2008)/ "Robotic Trocar Site Small Bowel Evisceration after Gynecologic Cancer Surgery," Journal of Obstetrics and Gynecology 112.2 Part 2, pp. 462-464, The American Obstetricians and Gynecologists. <http://journals.lww.com/greenjournal/Abstract/2008/08001/Robotic_Trocar_Site_Small_B>, abstract, one page, date viewed: Feb. 11, 2014.
Tonouchi, H., et al. (Nov. 1, 2004). "Trocar Site Hernia." JAMA Surgery 139 (11), American Medical Association, pp. 1248-1256. JAMA Networks, www.jamanetwork.com <http://www.jamanetwork.com>, (DOI: 10.1001/arch.surg.139.11.1248 JAMA Networks Web), nine pages, date viewed: Oct. 12, 2013.
Viju, S. (Jun. 2008). "Biodegradable Polyesters for Medical Applications." The Indian Textile Journal, vol. 118, Issue 9, p. 75: Features/Nonwoven and Technical Textiles., (ISSN 0019-6436), www.indiantextilejournal.com <http://www.indiantextilejournal.com>, two pages, date viewed: Feb. 20, 2014.
Wikipedia. Search: 'Electrospinning,' and 'Extracellular matrix', www.Wikipedia.org <http://www.Wikipedia.org>, 15 pages.
Yamamoto, M., et al. (Jan.-Mar. 2011). "Laparoscopic 5mm Trocar Site Herniation and Literature Review," Journal of the Society of Laparoendoscopic Surgeons, pp. 122-126, US National Library of Medicine National Institutes of Health (NCBI), www.PubMed.gov <http://www.PubMed.gov>, five pages, date viewed: Feb. 13, 2014.

\* cited by examiner

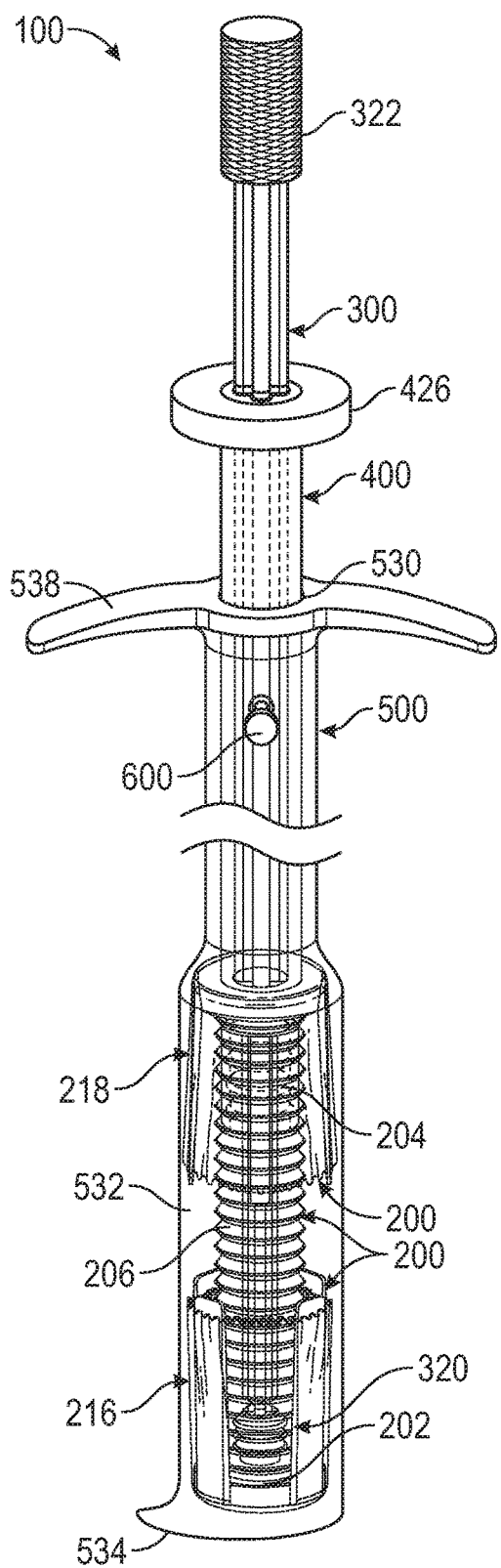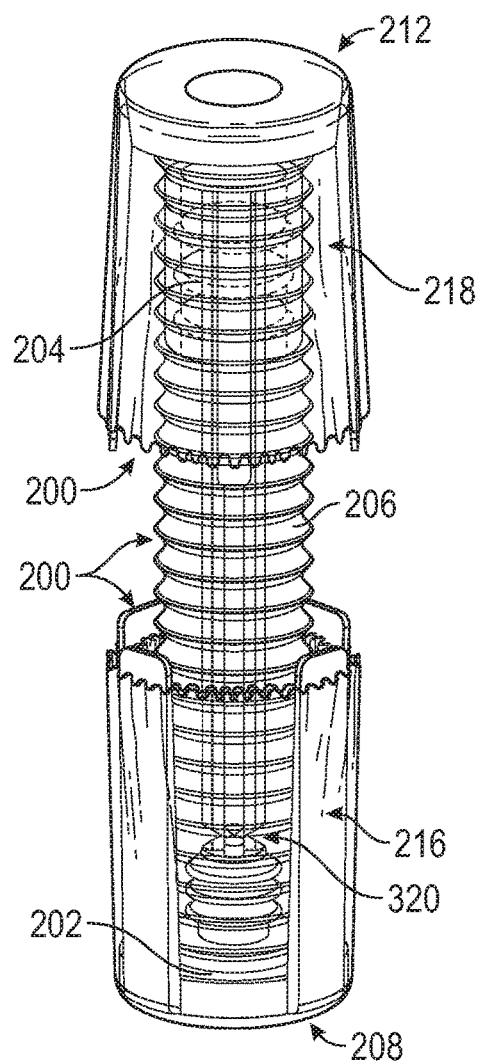
FIG. 1A
FIG. 1B

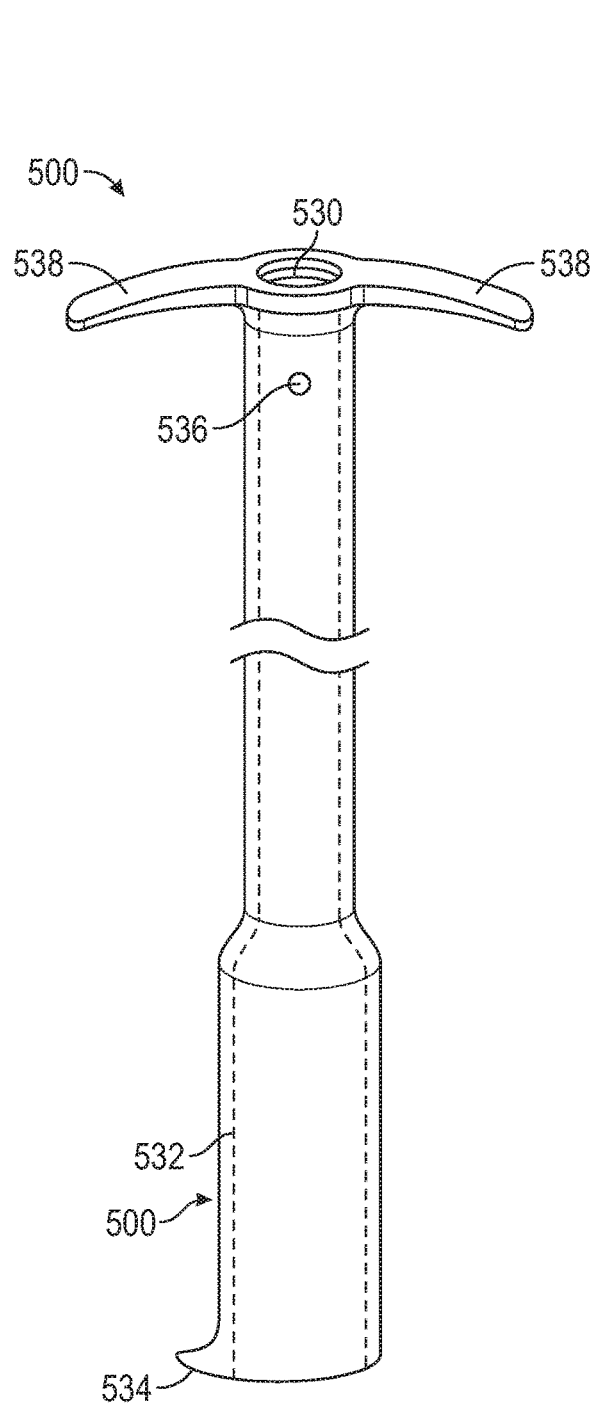
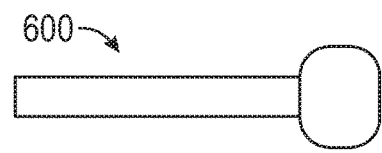
FIG. 5B
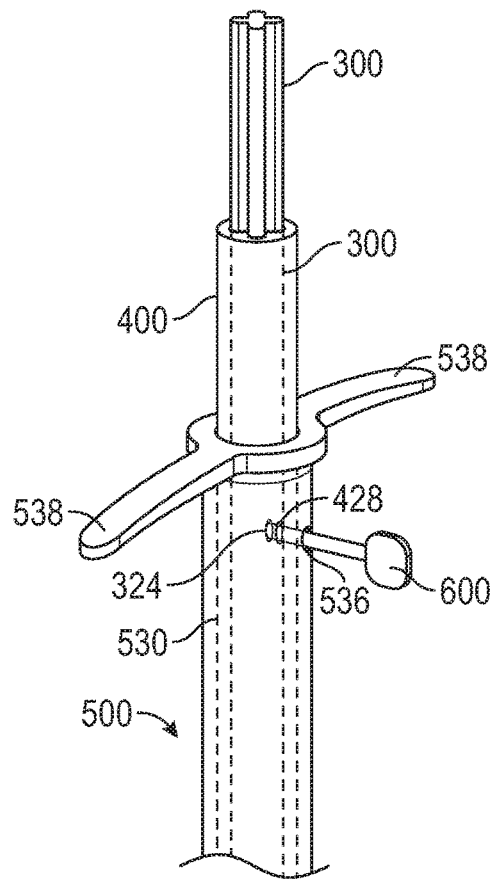
FIG. 5A
FIG. 5C

WOUND CLOSURE APPARATUS AND METHOD

CROSS-REFERENCE TO RELATED APPLICATION

This application is a Continuation-in-Part of U.S. patent application Ser. No. 16/275,222, filed Feb. 13, 2019; which is a Continuation-in-Part of U.S. patent application Ser. No. 15/449,818, filed Mar. 3, 2017 and published as U.S. Patent Publication No. 2017-0172552 on Jun. 22, 2017; which is a Divisional Application of U.S. Ser. No. 14/634,421, filed Feb. 27, 2015 and issued on Apr. 11, 2017 as U.S. Pat. No. 9,615,817, the contents of which are incorporated herein by reference in their entirety for all purposes.

FIELD OF THE DISCLOSURE

The present disclosure relates generally to a wound closure apparatus and method.

BACKGROUND OF THE DISCLOSURE

Minimally invasive surgery (MIS), also referred to as laparoscopic or endoscopic surgery, has experienced spectacular growth worldwide over the past few decades for the diagnosis and treatment of a variety of acute and chronic pathologies. Endoscopic procedures are economical, safer, and promote a more rapid recovery in contrast to conventional surgical approaches. Technological advancements in MIS are expected to have robust growth in the future. As endoscopic technologies develop and become the standard of care for most types of surgical interventions, the continued development of innovative quality tools to address the unique problems associated with this type of surgery must be vigorously pursued.

A laparoscopic surgery is performed by inserting a cannula (a hollow plastic or metal tube) through the abdominal wall, either by scalpel dissection or by blunt penetration with a piercing instrument (a trocar) occupying the central lumen of the cannula. When the cannula is placed through the skin and into the abdomen, the surgical blade or central trocar is withdrawn, leaving a cannula that is designed to inflate the abdominal cavity with carbon dioxide gas in order to distend the anterior abdominal wall away from the internal organs. The presence of this gas in the abdominal cavity is known as a pneumoperitoneum.

Once the pneumoperitoneum is established, a fiber optic endoscope (which may either be attached to a high-definition video camera or guided by direct vision) is inserted safely into the abdomen allowing visualization of the abdominal viscera. When complete visualization of the abdomen is accomplished, a number of secondary cannulae are placed via the previously described technique. The surgery is then performed through these cannulated passageways, referred to as ports. The ports function as conduits for the insertion and exchange of various specialized hand-held or robotic-assisted instruments and devices to accomplish the laparoscopic procedure, which would otherwise be performed by an open surgical incision.

The observed benefits of MIS include reduced blood loss, lower risk of infection, more rapid recovery rates, and reduced postoperative pain. These benefits have caused laparoscopy to become the preferred method for an ever-increasing number of surgical procedures. As with any other surgery, however, MIS is not without its share of complications. Two common complications relevant to MIS surgeries are the formation of abdominal adhesions and/or hernia development.

While laparoscopic adhesion formation occurs less frequently than those related to open surgeries, the risk remains omnipresent as a result of the cumulative effect of the fibrin-forming inflammatory process. Factors that predispose the development of adhesions include: ischemia (poor blood supply), obesity, malnutrition, diabetes, or the devascularization of the peritoneum caused by the surgery itself. The development of adhesions generally occurs between the fifth and seventh postoperative day, resulting in scar-like bands. These adhesive bands may surround the intestine and adhere them either together, or to the peritoneum of the interior abdominal wall. However, months to years later after the initial surgery, these constrictive bands may form a thickened fibrous web which, when fully compact, are capable of inflicting severe pain or causing an intermittent-to-complete bowel obstruction. These two unfortunate scenarios will likely translate into higher medical costs related to emergency surgical procedures, lengthy hospital admissions, and prolonged recovery periods.

The other complication related to minimally invasive procedures is the port-site wound hernia, also referred to as an incisional or ventral hernia. The port-site wound hernia is defined as the abnormal protrusion of abdominal viscera through the wound's fascial defect. This type of hernia commonly develops in the first four years after the index surgery. At present, there is a problematic lack of long-term data on the incidence and natural history of port-site hernia development. Significant contributing factors for port-site wound herniation relate to the size and location of the fascial defect.

Obese patients, with a body mass index (BMI) of thirty or greater, are more susceptible to port-site wound herniation regardless of the fascial defect's size. This may be attributed to the obese patient's enlarged pre-peritoneal space and/or tendency toward elevated intra-abdominal pressures. Extensive manipulation and stretching of the instrument port during the MIS procedure (i.e. retrieval of specimens, multiple re-insertions, or aggressive use of laparoscopic instruments or devices) may enlarge the size of the fascial defect beyond the wound's initial diameter thus rendering the fascial defect vulnerable to port-site wound herniation.

With regards to location, herniation occurs more frequently when the fascial defect is located in the midline of the abdomen, especially in the upper midline area or at the umbilicus, possibly due to the absence of supporting musculature in these areas. In contrast, port-site wound hernias occur less often when they are located below the umbilicus or more laterally on the abdomen.

Another contributing factor for the development of a port-site wound hernia is known as the Chimney Effect. This describes a partial vacuum that is created as the surgical cannula is withdrawn from the wound, much like a piston. As this negative pressure increases within the narrow perimeter of the wound, it is capable of drawing abdominal viscera through the fascial defect and in the subcutaneous tissue or out of the body, thus creating the port-site wound hernia.

There are two technical risk factors for port-site wound hernia: the surgical trocar design used for creating the wound, and/or the suture used for closing the fascial defect. With regards to the former, the bladed trocar presents a greater risk for port-site wound hernia development than non-bladed trocars. Port-site wound herniation may also be related to the repair of the fascial defect with suture, as exemplified by suture fractures, slipping of suture knots, excessive suture tension, or sutures that absorb too rapidly. Suture closure of these wounds can be time consuming and difficult whether the suturing method is performed by the traditional approach (a needle attached to a suture and operated by a needle holder held in the operator's hand), or by a contemporary method using wound closure devices. The latter generally incorporates a needle or sharp tool with a suture affixed to one end in order to approximate and close the fascial defect.

Regardless of the method, the application involves the same time-consuming and cumbersome approach for employing a needle (or sharp tool) with a suture affixed to one end in order to approximate and close the fascial defect within the narrow recesses of the port-site wound. Moreover, these suture techniques have the predictable risk of injuring the underlying bowel, omentum, or other organs as the needle is swept through the fascial tissues.

In obese patients these suturing methods can be painstakingly difficult, since the fascia is obscured from view by adipose tissue. If the fascial defect is too deep and/or is located at a steep angled trajectory in relation to its small skin incision, a blind attempt (e.g., with no direct vision) is the only option for closing the fascial defect. This risky suturing effort generally fails to capture a sufficient margin of the wound's edge.

With regards to the contemporary devices, they may share the same vexing difficulties as the traditional method. However, a specific drawback with these devices relates to their requirement for a pneumoperitoneum and direct visualization during their surgical application. This time-consuming requirement proves problematic, since all of these devices are unable to close the port operating the telescopic lens.

These technical challenges can compromise the wound's integrity, resulting in complications such as poor wound healing, suture failure, and port-site wound herniation, all of which will inadvertently negate the advantages of the MIS procedure. Ultimately, these complications will lead to increased pain and loss of productivity for the patient, while at the same time reducing efficiency with increased costs to the health care system in general.

SUMMARY OF THE DISCLOSURE

Since the advent and proliferation of minimally invasive surgeries there has been a longstanding need for a rapid, safe and effective means of closing the strongest and most complete tissue layer of the port-site wound, specifically the anterior fascia of the abdominal wall. Embodiments of the disclosure are directed to an apparatus and method for the optimal closure of minimally invasive port-site wounds that, in contrast to traditional and contemporary approaches for closing the fascial defect, include enhancements to prevent complications while facilitating wound healing.

By virtue of its unique one-piece design, the apparatus can function as its own insertion device, deployment tool, and highly sophisticated tissue engineered implant. Regenerative medicine may play a role in the development of the wound plug's bio-chemical properties by exhibiting characteristics that, when exposed to living tissues of the body, may not cause damage or adverse biological reactions (e.g., it may be biocompatible); may physiologically degrade and may be absorbed during a specific period of time (e.g., it may be bioabsorbable); and may be completely eliminated by the body's natural processes with no residual side effects (e.g., it may be bioresorbable). These essential characteristics may synergistically regenerate and heal the damaged tissues of the wound. The process can sustain the wound plug's durability and strength for the period of time deemed necessary for the wound plug to be absorbed by the body as the new tissues take its place. In this way, the apparatus can effectively, safely, and easily seal and close the fascial defect of the port-site wound.

The apparatus can be inserted and deployed within any size, depth or angle of port-site wound. Due to its highly versatile design, the apparatus can accurately locate the anterior abdominal fascia surrounding the fascial defect. The apparatus can ensure optimum application and deployment of its wound plug without necessitating the use of any surgical cannula, pneumoperitoneum, or telescopic lens to aid in its insertion, delivery, or deployment.

The apparatus can secure closure of the fascial defect by deployment of a unidirectional ratchet-rivet mechanism that engages the tissues of the fascial defect gently between two rivet heads. The apparatus can be deployed above, below, and within the anterior fascial defect, causing the defect to become gently sandwiched within the non-traumatic clamping force of the apparatus's wound plug. This three-dimensional approach for closing and sealing the defect echoes three basic tenets proposed in hernia mesh science. The first is the apparatus's suprafascial rivet head, which can secure the anterior fascial defect from above as an overlay. The second is the apparatus's subfascial rivet head, which can affix below the defect as an underlay. The third tenet can be achieved by the inlay position of the wound plug's shape memory column (stationed between the two rivet heads) that can fill and seal the void from within the fascial defect. The column can be compressible to fill any size wound and to keep body tissue from entering the wound. Further, it can fill in any gaps to prevent the other elements of the wound plug from shifting.

The tissues of the fascial defect may not be strictly fixed by the apparatus, which significantly reduces the detrimental effects of tissue ischemia (poor blood supply) or necrosis (tissue death) within the wound. The wound plug can spread over a wide surface area, beyond the circumference of the wound, to secure and promote tissue adherence and cellular growth. Another benefit of the wound plug's comprehensive overlay, underlay and inlay of the fascial defect and surrounding tissues is to prevent the plug from migrating or dislodging from its deployed position.

The straightforward and simple application of the apparatus may greatly reduce operating room expenditures in time, efficiency and labor; reduce risk of future adhesions and herniation; facilitate healing and regeneration of the tissues; reduce pain in the patient; and promote optimal patient outcomes with a rapid recovery rate. The apparatus may incorporate a wound plug that, by virtue of its varied chemical and biological composition, may be capable of providing structural and mechanical support for the ingrowth and regrowth of native tissues by interacting with the body's natural intra-cellular processes vital for wound healing.

BRIEF DESCRIPTION OF THE DRAWINGS

For a better understanding of the various described embodiments, reference should be made to the Detailed Description below, in conjunction with the following drawings in which like reference numerals refer to corresponding parts throughout the figures.

FIG. 1A-1B illustrate the wound closure apparatus according to embodiments of the disclosure.

FIGS. 5A-5C illustrate a shield according to embodiments of the disclosure.

DETAILED DESCRIPTION

Figure 2A:
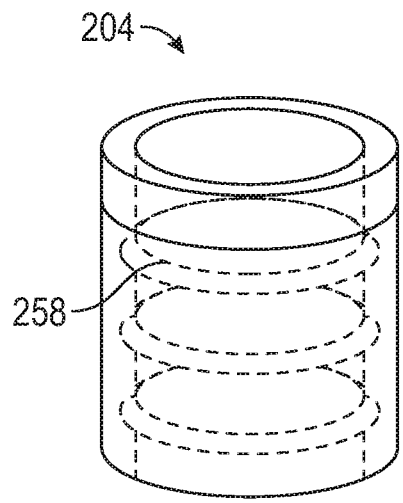
FIGS. 2A-2N illustrate the wound plug according to embodiments of the disclosure.
Figure 2B:
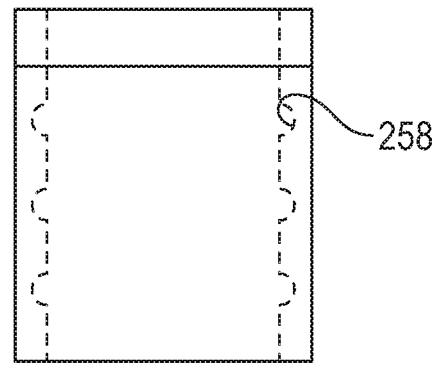
Figure 2C:
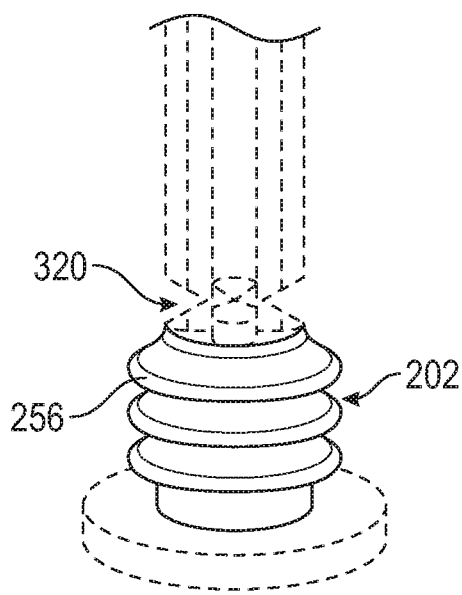
Figure 2D:
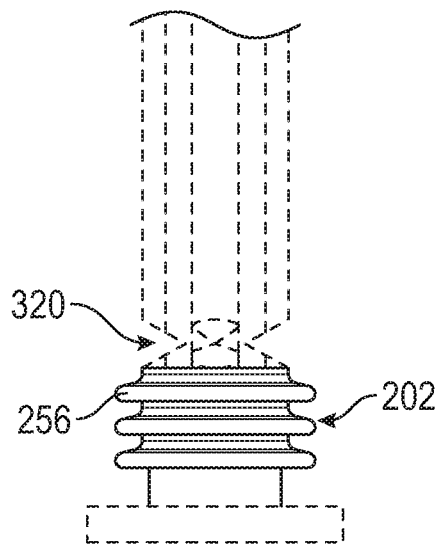

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Since the advent and proliferation of minimally invasive surgeries there has been a longstanding need for a rapid, safe and effective means of closing the strongest and most complete tissue layer of the port-site wound, specifically the anterior fascia of the abdominal wall. Embodiments of the disclosure are directed to an apparatus and method for the optimal closure of minimally invasive port-site wounds that, in contrast to traditional and contemporary approaches for closing the fascial defect, include enhancements to prevent complications while facilitating wound healing.

By virtue of its unique one-piece design, the apparatus can function as its own insertion device, deployment tool, and highly sophisticated tissue engineered implant. Regenerative medicine may play a role in the development of the wound plug's bio-chemical properties by exhibiting characteristics that, when exposed to living tissues of the body, may not cause damage or adverse biological reactions (e.g., it may be biocompatible); may physiologically degrade and may be absorbed during a specific period of time (e.g., it may be bioabsorbable); and may be completely eliminated by the body's natural processes with no residual side effects (e.g., it may be bioresorbable). These essential characteristics may synergistically regenerate and heal the damaged tissues of the wound. The process can sustain the wound plug's durability and strength for the period of time deemed necessary for the wound plug to be absorbed by the body as the new tissues take its place. In this way, the apparatus can effectively, safely, and easily seal and close the fascial defect of the port-site wound.

The apparatus can be inserted and deployed within any size, depth or angle of port-site wound. Due to its highly versatile design, the apparatus can accurately locate the anterior abdominal fascia surrounding the fascial defect. The apparatus can ensure optimum application and deployment of its wound plug without necessitating the use of any surgical cannula, pneumoperitoneum, or telescopic lens to aid in its insertion, delivery, or deployment.

The apparatus can secure closure of the fascial defect by deployment of a unidirectional ratchet-rivet mechanism that engages the tissues of the fascial defect gently between two rivet heads. The apparatus can be deployed above, below, and within the anterior fascial defect, causing the defect to become gently sandwiched within the non-traumatic clamping force of the apparatus's wound plug. This three-dimensional approach for closing and sealing the defect echoes three basic tenets proposed in hernia mesh science. The first is the apparatus's suprafascial rivet head, which can secure the anterior fascial defect from above as an overlay. The second is the apparatus's subfascial rivet head, which can affix below the defect as an underlay. The third tenet can be achieved by the inlay position of the wound plug's shape memory column (stationed between the two rivet heads) that can fill and seal the void from within the fascial defect. The column can be compressible to fill any size wound and to keep body tissue from entering the wound. Further, it can fill in any gaps to prevent the other elements of the wound plug from shifting.

The tissues of the fascial defect may not be strictly fixed by the apparatus, which significantly reduces the detrimental effects of tissue ischemia (poor blood supply) or necrosis (tissue death) within the wound. The wound plug can spread over a wide surface area, beyond the circumference of the wound, to secure and promote tissue adherence and cellular growth. Another benefit of the wound plug's comprehensive overlay, underlay and inlay of the fascial defect and surrounding tissues is to prevent the plug from migrating or dislodging from its deployed position.

The straightforward and simple application of the apparatus may greatly reduce operating room expenditures in time, efficiency and labor; reduce risk of future adhesions and herniation; facilitate healing and regeneration of the tissues; reduce pain in the patient; and promote optimal patient outcomes with a rapid recovery rate. The apparatus may incorporate a wound plug that, by virtue of its varied chemical and biological composition, may be capable of providing structural and mechanical support for the ingrowth and regrowth of native tissues by interacting with the body's natural intra-cellular processes vital for wound healing.

Apparatus

FIGS. 1A-1B illustrate a wound closure apparatus 100 according to embodiments of the disclosure. The apparatus can be a self-contained device for delivery and deployment of a tissue engineered wound plug 200 that can secure fascial closure of laparoscopic port-site wounds. The wound plug 200 can include a subfascial rivet head 202, a suprafascial rivet head 204, and a compressible column 206, wherein the compressible column surrounds and is coupled to each of the subfascial rivet head and the suprafascial rivet head.

The apparatus may include a post 300, a rod 400, and a shield 500 for delivery and deployment of the wound plug 200. The post 300 can include the subfascial rivet head 202 at a first end of the post and a handle 322 at a second end of the post. The rod 400 can have a rod cavity 466 through which the post 300 is positioned. A first end of the rod 400 can be in contact with the suprafascial rivet head 204 of the wound plug 200, and the rod can include a plate 426 at a second end of the rod. The shield 500 can contain portions of the wound plug 200, the post 300, and the rod 400 in a shield cavity 530.

Once in the wound, these components can deploy the wound plug 200 with the subfascial rivet head 202 below the fascia 750 of the wound and the suprafascial rivet head 204 above the fascia of the wound 748. As this occurs, the column 206 of the wound plug 200 can be stationed within the opening of the wound. Once the wound plug 200 is secured above, below, and within the fascial defect, the two components of the rivet heads 202 and 204 may be interlocked within an inner channel 260 of the column 206. As a result, the wound plug 200 may be implanted into the port-site wound's fascial defect, while the post 300, the rod 400, and the shield 500 may be removed from the wound and safely discarded.

The apparatus's design, consisting of its own deployment device and implant, creates a mechanical symbiosis that precludes the need for any other additional accessories (e.g., other tools or instruments), or conditions of the wound (e.g., pneumoperitoneum, telescopic visualization, wound retraction, or increasing the length of the skin incision).

Wound Plug

Figure 2E:
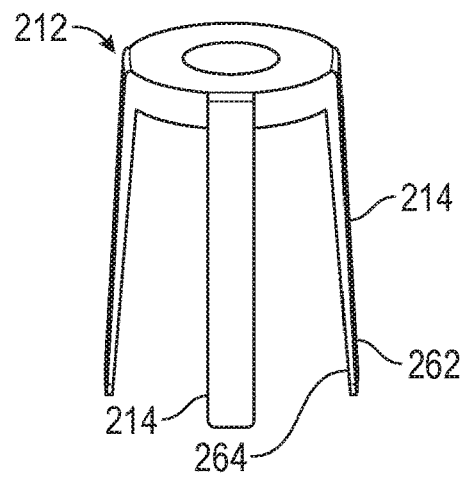
Figure 2E:
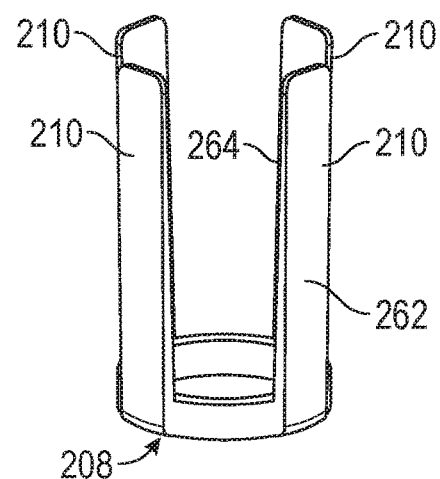
Figure 2F:
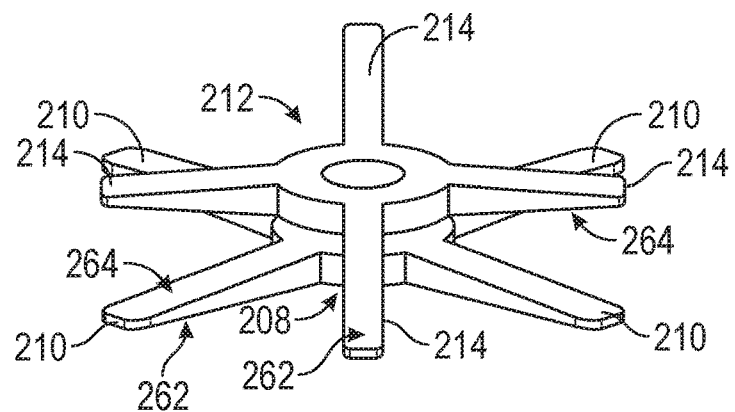
Figure 2G:
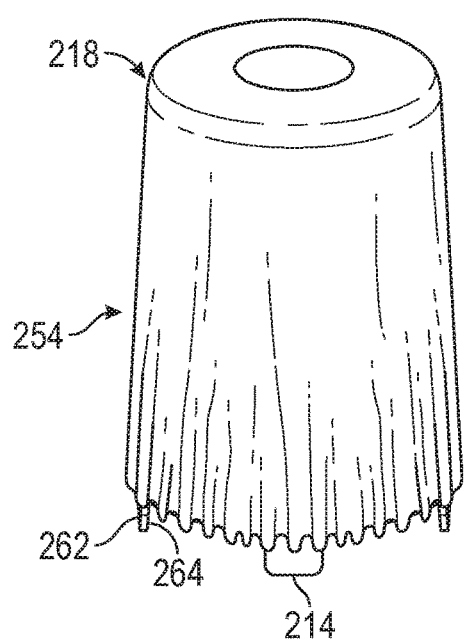
Figure 2H:
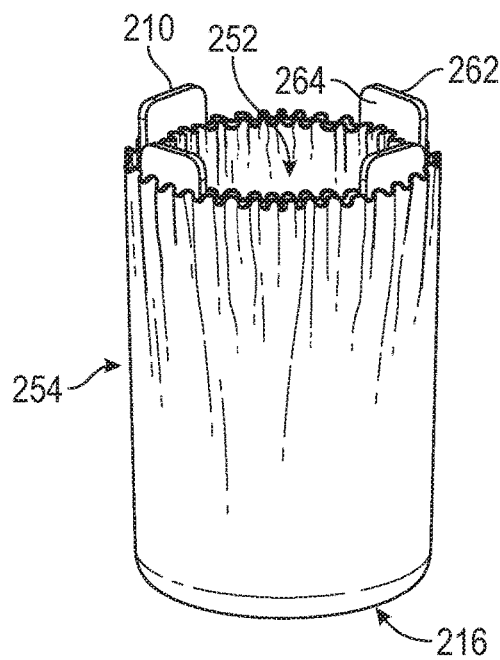
Figure 2I:
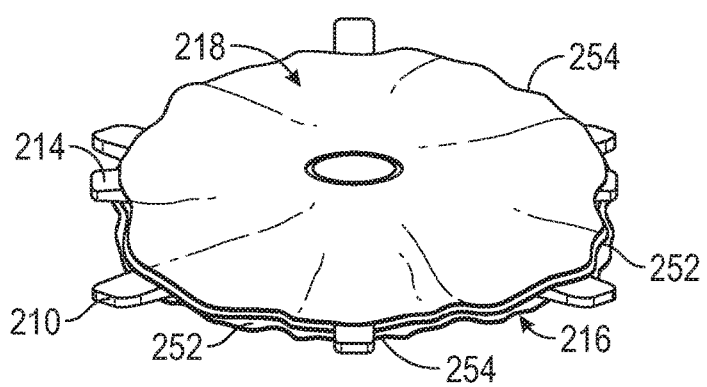
Figure 2J:
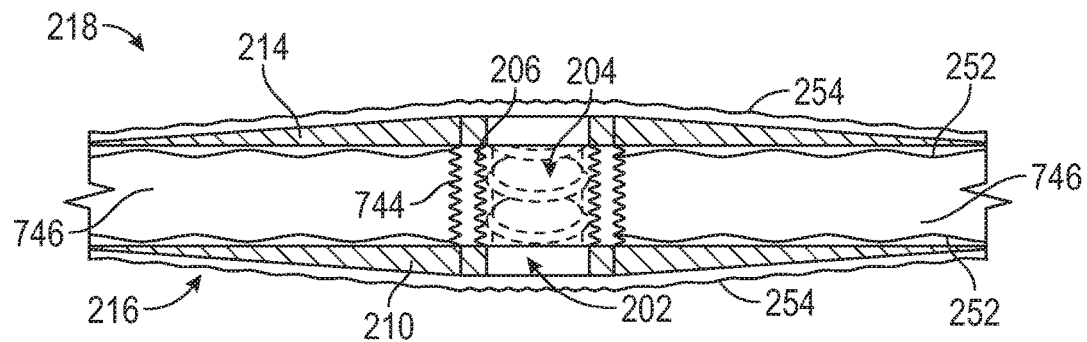
Figure 2K:
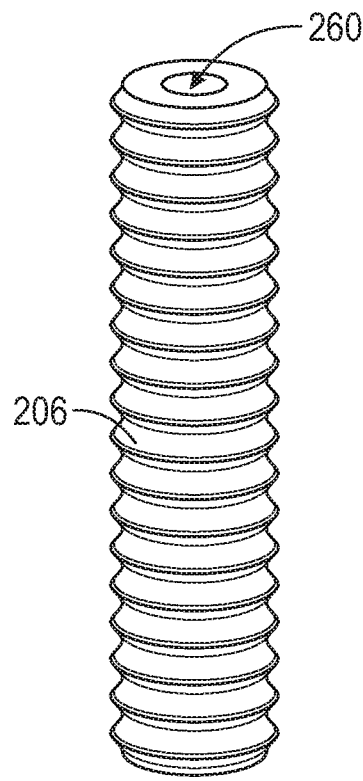
Figure 2L:
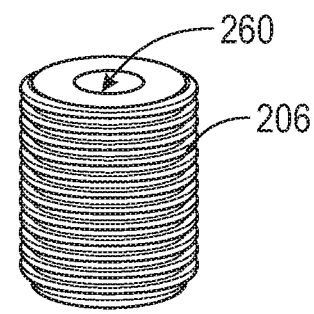
Figure 2M:
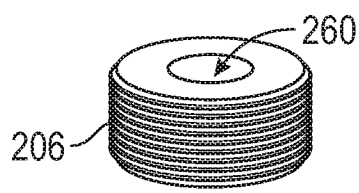
Figure 2N:
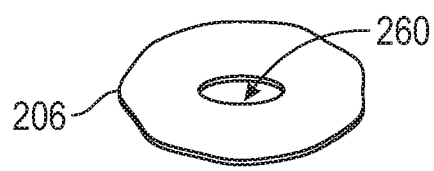

FIGS. 1B and 2A-2N illustrate a wound plug 200 according to embodiments of the disclosure. In some embodiments the wound plug includes a subfascial rivet head 202, a suprafascial rivet head 204, and a compressible column 206. In some embodiments, the subfascial rivet head 202 includes a subfascial extension 208 comprising a plurality of stays 210, and the suprafascial rivet head 204 includes a suprafascial extension 212 including a plurality of stays 214. In some embodiments, the wound plug 200 further includes a subfascial biohybrid scaffold 216 coupled to the subfascial extension 208 and a suprafascial biohybrid scaffold 218 coupled to the suprafascial extension 212.

FIGS. 2A-2D illustrate subfascial and suprafascial rivet heads 202 and 204 according embodiments of the disclosure. The rivet heads 202 and 204 may be composed of natural polymers or copolymers like chitosan, gelatin, alginate, collagen and/or other wound healing promoters; as well as synthetic polymers or copolymers such as Polyglycolide (PGA), Polylactide (PLA), Polydioxanone (PDO), Polycaprolactone (PCL), or synthetic copolymers like L-lactide-co-glycolide (PLGA). The possibilities for such fabrication techniques may include but are not limited to polymeric blends, dip coating, adhesive layering, copolymerization, grafting, homogeneous mixtures, and/or electrospinning for creating a biosynthetic composite material.

This skeletal architecture can be manufactured from a polymeric composite for superior tissue engineering. A synthetic polymer or copolymer may be desirable because it demonstrates mechanical and physiochemical characteristics similar to those of the biological tissue it will temporarily replace. Additionally, synthetics can be tailored to control their microstructure and degradation rate. In contrast, however, natural polymers can have bioactivity-possessing growth factors and pertinent signals that may facilitate cellular adhesion, growth, and proliferation. Consequently, the strength of the former, and the bioactivity of the latter may mutually provide intrinsic benefits while diminishing each other's deficiencies.

The semi-rigid polymer composite of this skeletal architecture can be designed with microscopic perforations, which provide a gradient through which the native tissue cells may proliferate. As the device degrades within the body these perforations may be critical for tissue adherence and optimal cellular response and healing. Moreover, a natural polymer may be adhered as a layer upon the synthetic polymer construct.

The subfascial rivet head 202 may be a part of the post 300 at a first end of the post, separated from the rest of the post by a breakaway point 320. The post 300 can be used to position the subfascial rivet head 202 below the fascia 750 into the pre-peritoneal space, and the post can be broken at the breakaway point 320 to separate the subfascial rivet head 202 from the rest of the post after the wound plug 200 is deployed in its entirety.

In some embodiments, the subfascial rivet head 202 may comprise an engaging ratchet configured to engage with a hollow receiving pawl of the suprafascial rivet head 204. For example, the engaging ratchet may include a number of flanges 256 configured along its exterior that correspond to a number of reciprocal annular grooves 258 within the interior of the receiving pawl. Once the rivet heads 202 and 204 are deployed, the subfascial and suprafascial portions of the wound plug 200 become interlocked by deployment of the unidirectional mechanism.

In some embodiments, the suprafascial rivet head 204 may comprise a hollow receiving pawl configured to engage with an engaging ratchet of the subfascial rivet head 202. For example, the receiving pawl may include a number of reciprocal annular grooves 258 configured within its interior that correspond to a number of flanges 256 on the exterior of the engaging ratchet. Further, the suprafascial rivet head 204 may be configured with a channel to allow the post 300 to pass through its hollow core.

In some embodiments, engagement of the subfascial and the suprafascial rivet heads 202 and 204 may be confirmed by three audible clicks synchronized with three tactile sensations. These effects confirm that the reciprocal annular grooves 258 of the receiving pawl have successfully interlocked with the flanges 256 of the engaging ratchet.

In some embodiments, extensions 208 and 212 surround the outer perimeters of each rivet head 202 and 204. For example, FIGS. 2E-2F illustrate each extension 208 and 212 including a plurality of stays 210 and 214. In some examples, the number of stays on each rivet head can be chosen relative to the size of each rivet head extension 208 and 212, as well as to the weight and size of their associated biohybrid scaffold 216 and 218. The cross sectional profile of each stay may be tapered on one side 262 and non-tapered (e.g., flat) on the opposing side 264. This profile can be consistent throughout the length of each stay, terminating into a blunt-point end.

The stays 210 and 214 may be fabricated using shape memory properties, allowing for two different configurations during the implant's surgical application. Prior to deployment, the stays may project at 90° angles from the outer perimeter of each rivet head, offset relative to each other at a 45° angle of arc. In this second configuration, the stays may be superiorly and inferiorly convergent as they enclose an outer wall of the column 206 in an alternating fashion. Further, each stay may include two distinct surfaces 262 and 264. Within the apparatus 100, a first non-tapered surface 264 may be adjacent to the wall of the column 206, whereas a second tapered surface 262 may encircle an outer perimeter of the column 206 exteriorly.

Once the rivet heads 202 and 204 are deployed, however, the shape memory properties of the stays 210 and 214 can be immediately affected by the body's temperature and/or pH relative to a pre-determined time interval also inherent in their chemical properties. These physical and biological properties can cause each stay to automatically deploy its corresponding biohybrid scaffold (e.g., biohybrid scaffolds 216 and/or 218) into a full radial expansion above and below the fascial defect, thus orienting the stays' non-tapered surfaces 264 toward the abdominal fascia, while their tapered surfaces 262 are adjacent to the native tissues surrounding the port site wound (e.g., native tissues 768 in FIGS. 6C and 6D).

Although FIG. 2E illustrates just the subfascial extension 208 including the plurality of stays 210, in some embodiments, the subfascial extension 208, the plurality of stays 210, the subfascial rivet head 202, and the post 300 are all formed of a single piece. Further, although FIG. 2E illustrates just the suprafascial extension 212 including the plurality of stays 214, in some embodiments, the suprafascial extension 212, the plurality of stays 214, and the suprafascial rivet head 204 are all formed of a single piece.

In some embodiments, the rivet heads 202 and 204 may include a disc shape as illustrated in the figures. In some embodiments, the rivet heads may alternatively include other shapes, such as rectangular, oval, hexagonal, octagonal, star, square, etc.

In some embodiments, the rivet heads 202 and 204 may be manufactured from the same shape memory blend of natural and synthetic polymers (or copolymers) as the extensions 208 and 212. In this way, the rivet heads can change to a smaller or more compact profile, such as a cone or ball.

In some embodiments, the stays 210 and 214 may be profiled to be tapered or non-tapered, thick or thin, wide or narrow, etc. In some embodiments, the stays may be profiled in such a way that their central convergence forms the receiving pawl and engaging ratchet. In this embodiment, the stays may be configured in linear geometric shapes (i.e., spokes on a bicycle wheel, or a lattice-like network), or as a mosaic of crisscrossing curves (i.e., lace-like or snowflake designs) for establishing the skeletal framework of the rivet heads 202 and 204, as well as the rivet head extensions 208 and 212.

Although embodiments of the disclosure are described in terms of rivet heads comprising a receiving pawl and an engaging ratchet, embodiments are not so limited. Other embodiments are contemplated for attaching the suprafascial and subfascial portions of the wound plug 200, such as superior and inferior clasps, mechanical fasteners, crimp engagements, mechanical latches, suture tie(s) with a type of slip knot(s), post or bead-like snaps, a tapering pin that engages within a narrowing hole, hook and eye attachments, a type of buckling apparatus, or even a chemical tissue adhesive disseminating from the column 206.

FIGS. 2G-2J illustrate biohybrid scaffolds 216 and 218 according to embodiments of the disclosure. In some embodiments, the scaffolds 216 and 218 may comprise a collagen rich acellular non-crosslinked tissue sheet that is replete with vital components for wound healing, such as laminin, biometric proteins, carbohydrates, etc. When these multi-layered tissue sheets are applied to a wound site, a synergy between its scaffold and the native tissues can develop, causing specialized living cells to proliferate and regenerate new tissue into the wound site.

In some embodiments, the biohybrid scaffolds 216 and 218 include two distinct surfaces. A first surface 252, the lamina propria layer, may be conducive for tissue regeneration and healing. In contrast, the second surface 254, the epithelial basement membrane, may be beneficial as a collagen rich tissue scaffold. The scaffolds may be deployed such that the first surface 252 is in contact with the abdominal fascia around the fascial defect 748 and 750, while the second surface 254 is in contact with surrounding native tissues of the wound (e.g., native tissues 768 in FIGS. 6C and 6D).

In some embodiments, the biohybrid scaffolds 216 and 218 may cover and embed only the flatter, larger surfaces of the rivet heads 202 and 204 and both sides of each of the stays 210 and 214 with the exception of the stays' distal blunt ends. The scaffolds 216 and 218 may include centralized openings to allow portions of the rivet heads 202 and 204 and the vertical axis of the post 300 to pass through the centers of the scaffolds.

In some embodiments, an electrospun layer may be applied between the tissue surfaces of each biohybrid scaffold 216 and 218 directly contacting the shape memory components of the stays 210 and 214. This may further promote cohesiveness between the two layers for strength and manageability.

Prior to deployment biohybrid scaffolds 216 and 218 can conform to the same constricted configuration presented by the embedded stays 210 and 214. In this deformed profile, the lamina propria layer 252 can be adjacent to the wall of the column 206, while the epithelial basement membrane 254 can encircle the column exteriorly. In this pre-deployment profile, the scaffold tissue sheets may appear as multiple vertical pleats, in the likeness of a pleated paper coffee filter, although pleats may be more rounded or larger in nature.

Once the rivet heads 202 and 204 are deployed, the bio-reactivity of the surrounding stays 210 and 214 can simultaneously spread its corresponding biohybrid scaffold 216 and 218 into full radial expansion. As a result, the lamina propria layer 252 that encases the inner (fascial) surfaces of the rivet heads and stays (e.g., the non-tapered surfaces 264) may be juxtaposed to one another as they cover the subfascial and suprafascial surfaces 750 and 748 surrounding the wound 744. Further, the epithelial basement membrane 254 covering the exterior sides of the rivet heads and the tapered surfaces 262 of the stays can buttress the surrounding native tissues (e.g., native tissues 768 in FIGS. 6C and 6D). Consequently, following deployment each rivet head's outer diameter may be large enough to thoroughly cover both sides of the defect.

In some embodiments, the scaffolds may be produced with other types of biological or synthetic (absorbable or nonabsorbable) scaffolding materials.

In some embodiments, the skeletal framework of the rivet heads and the stays may not be included, and instead the shape memory biohybrid scaffolds of each rivet head may be resilient enough to deform into a pre-deployment configuration without the necessity of any supportive skeletal framework.

In the absence of the skeletal framework, it may be beneficial for a tissue adhesive to be dispersed from the column 206 to cause the two biohybrid scaffolds to adhere locally to the wound. If a tissue adhesive is used for securing the wound plug to the wound, there may be no need for a mechanical fixation apparatus such as an engaging ratchet or a receiving pawl. As a result, this alternative suggests only a simple open-ended central opening within the suprafascial rivet head 204. Likewise, the post 300 may be a plain shaft (without an engaging ratchet or a breakaway point 320). The distal end of the post may need to be tenuously anchored to the electrospun network within the two layers 252 and 254 of the subfascial biohybrid scaffold 216 covering the subfascial rivet head 202. After deployment, and the local tissue adhesive from the column 206 is dispersed, the terminal end of the post may be twisted, torqued, pulled, or snapped from its temporary electrospun attachments within the subfascial biohybrid scaffold of the subfascial rivet head.

In some embodiments, the biohybrid scaffold 216 and 218 may be uniform, and may have wide or narrow shapes that may include oval, rectangular, star-like or flower-petal projections, etc. In some embodiments, the subfascial and suprafascial biohybrid scaffolds may be profiled in two entirely different geometric shapes and widths. Further, each scaffold may be fabricated from identical biological or chemical properties to that of other elements of the wound plug 200.

FIGS. 2K-2N illustrate a compressible column 206 according to embodiments of the disclosure. The column 206 may be a highly porous shape-memory structure, in the form of a sponge or foam, which provides a large surface area to promote cellular ingrowth, uniform cellular distribution, and neovascularization. The column may be centered between the two rivet heads 202 and 204. Prior to deployment, the receiving pawl and the engaging ratchet may be recessed within an inner channel 260 of the column. In some embodiments, the column may further include an electrospun network between the terminal borders of the column and the fascial surfaces 252 of the biohybrid scaffold 216 and 218 to achieve an integrated fusion between these structures, thus uniting them together as a single unit. As a result, the column's inferior section may be deployed in unison with the subfascial rivet head 202, while the superior portion of the column may be deployed with the suprafascial rivet head 204. After deployment, the column's initial tube-like profile may be positioned within the border of the wound.

The wall of the column 206 may be constructed with multiple compact circumferential pleats, such that the column compresses in an accordion-like fashion as the subfascial and suprafascial portions of the wound plug become interlocked. Accordingly, the length of the column compresses while maintaining its outer diameter so as to not interfere with the interlocking of the rivet heads.

In some embodiments, once the pleats are mechanically compressed, the body's temperature and/or pH can affect shape memory properties of the column 206, causing the column to automatically expand and pervade the interior of the wound in a washer-like profile with an outer diameter that does not fill the central defect. This smaller diameter of the column's washer-like profile can allow for the porous network to absorb blood and body fluids, increasing in size to swell and pervade the wound like a seal. The final configuration of the column, therefore, may fill the central defect like a low-pressure seal or plug without exerting pressure on the bordering tissues of the wound. As a result of this seal, the inner channel 260 of the column may become completely obliterated, thus resulting in an adherence between the column and the engaged components of the rivet heads 202 and 204. The benefit of this adherence is that dead space and vacuums are averted within the interior of the wound plug 200, thereby encouraging tissue regeneration.

In some embodiments, the size, distribution, volume, shape, and roughness of pores within the column 206 may have a powerful influence on cellular penetration and growth. Further, the pores may be interconnected in order to facilitate the essential transfer of oxygen, nutrients, and other physiochemical elements and biological exchanges to and from the living cells.

In some embodiments, the porous structure of the column 206 may be saturated with either a bioactive cellular matrix powder or a biocompatible hydrogel. Saturating the column with one or more of these materials can promote a synergistic interplay between it and the surrounding native tissues of the port-site wound. Additionally, the column's porous construction can incorporate pharmaceutical enhancements into its design, such as tissue adhesives, stem cell recruitment adjuncts, regenerative biochemical factors, insulin growth factor, anesthetic or antibiotic time-released drugs, etc.

In some embodiments, the inner channel 260 of the column 206 surrounding the post 300 and portions of the rivet heads 202 and 204 may be filled with a tissue-healing hydrogel or liquefied state of the same. Following deployment, the locally applied tissue adhesive may be dispersed from the column to function as a chemical securing mechanism for sealing the wound plug to the wound. In some embodiments, the column 206 itself may be made of the hydrogel with an outer wall made of denser gelatinous material (or skin) which encases the more viscous and/or liquefied form.

In some embodiments, the column 206 may include a finely shredded or spider web-like form of the bioactive acellular tissue matrix and/or liquefied form of the same. In some embodiments, the column may be fabricated from any number of materials including a sponge, foam, hydrogel, acellular pig bladder xenograft, any other type of xenografts, synthetic-absorbable scaffolding material, or any combination of these options. In some embodiments, the column may occur as a hollow chamber (i.e., a small bladder) formed by either a xenograft or other type of tissue engineered material that may contain pharmaceutical and bioactive substances, hydrogel, and/or the possibility of a tissue adhesive within its interior.

In some embodiments, the column 206 may be formed by stacking multiple centrally-perforated washers, one on top of the other, around the post 300 and the mechanical securing mechanisms of the rivet heads 202 and 204.

In some embodiments, the pleats of the column 206 may be arranged in vertical columns, or curving these vertical columns into a spiraling, candy cane-like design. By arranging the folds or pleats in these configurations, the column may compress like a collapsed spring. Moreover, it may be advantageous to cut these vertical or horizontal lines rather than utilizing pleats and/or folds within the wall of the column. Additionally, a combination of cuts and/or pleats or folds may contribute to a more successful compression for the column during deployment.

Delivery and Deployment Apparatus

The post 300, the rod 400, and the shield 500 form an apparatus 100 for delivery and deployment of the wound plug 200. These three components may reside at different radial levels in the apparatus. The post 300 may be located in the core of the apparatus and may be the longest of the three components, with its handle 322 rising higher than the other two components. The rod 400 surrounds portions of the post 300 and includes a plate 426 at one end (e.g., approximately midway between the handle 322 of the post 300 and grips 538 of the shield 500). The shield 500 surrounds portions of the rod 400 and the post 300 in its shield cavity 530. The shield includes an implant chamber 532 that contains portions of the wound plug 200 before deployment. Each of the post, the rod, and the shield may include an alignment pin hole through which an alignment pin 600 may be placed to align the various components with respect to each other. The alignment pin 600 may be removed prior to deployment, as described below.

In some embodiments, each of the post 300, the rod 400, and the shield 500 may be made of synthetic polymers without the essential blends of polymer composites comprising the wound plug 200. As a result, the overall rigid construction of these elements (e.g., the elements that will not be implanted within the body) may be fabricated from non-critical, bio-safe materials. Once the post, the rod, and the shield are separated from the wound plug and removed from the wound, their byproducts may be safely discarded as environmentally friendly, non-toxic wastes.

Figures 3A, 3B:
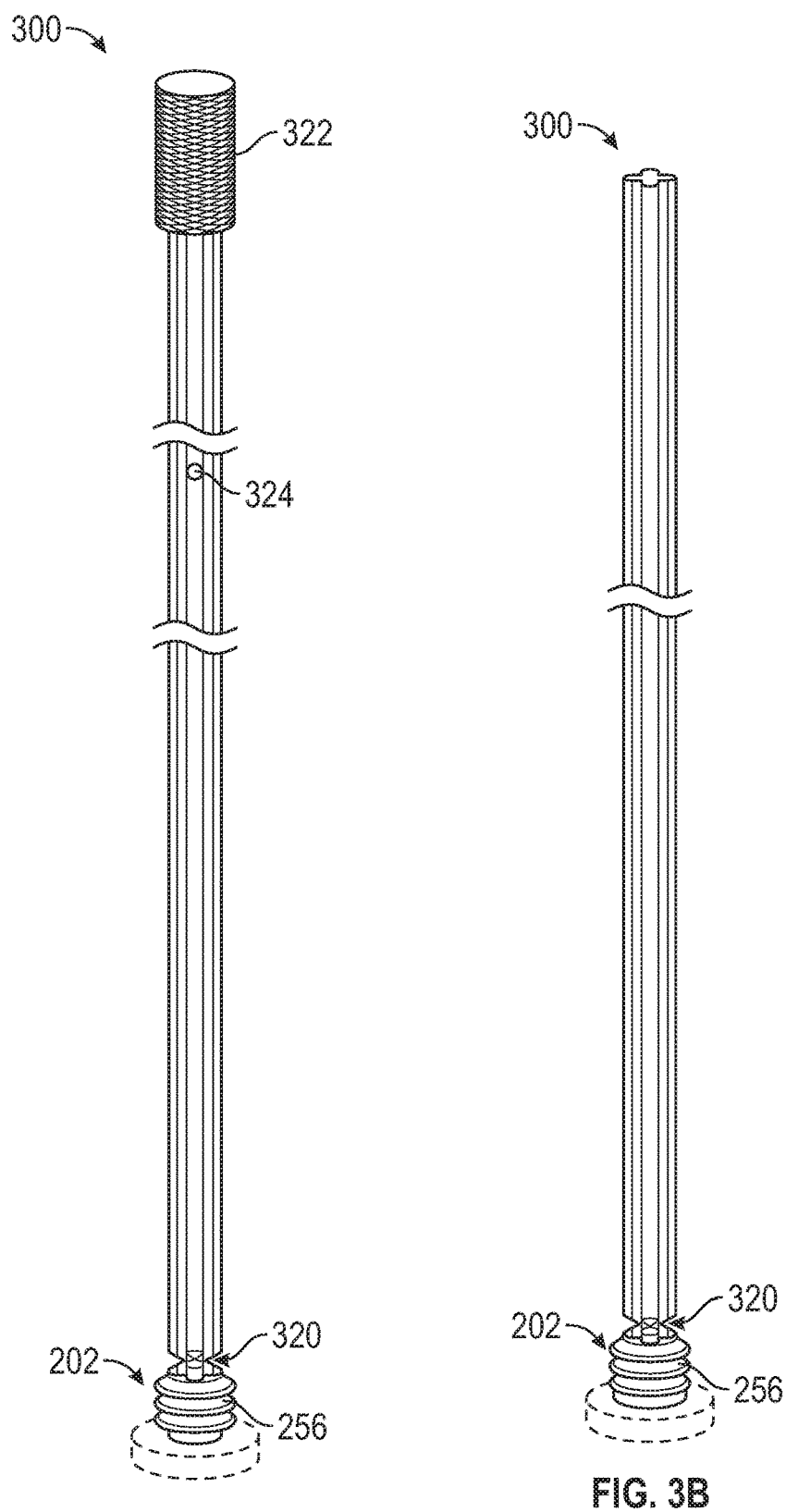
FIGS. 3A-3B illustrate a post according to embodiments of the disclosure.

FIGS. 3A-3B illustrate a post 300 according to embodiments of the disclosure. The post may be a vertical and most internal axis by which all the components of the apparatus 100 may be collectively aligned and integrated for deployment. In this unique position, the post may traverse proximally throughout a series of internal conduits of the column 206 (e.g., the inner channel 260 of the column), the suprafascial rivet head 204, the rod 400 (e.g., the inner channel 466 of the rod), and the shield 500 (e.g., the shield cavity 530). The alignment of these cannulated components can create a common passageway through which portions of the post 300 can move.

The post 300 may be an injected molded structure comprised of several diverse profiles along its vertical construct, including a subfascial rivet head 202 (e.g., the engaging ratchet) at a first end, and a handle 322 at a second end. The post may further include a breakaway point 320 between the subfascial rivet head and the handle. The breakaway point distinguishes the portion of the post included in the wound plug (i.e., the subfascial rivet head) from the rest of the post. In some embodiments, the breakaway point 320 may be configured to provide vertical stability and strength, thereby resisting compression or elongation during insertion and deployment. However, following the application of minimal twisting torque to the handle 322, the post 300 can break at the breakaway point.

In some embodiments, the post 300 retains a cruciate profile until it transitions into the inferior flanges 256 and distal base of the engaging ratchet. Although the subfascial rivet head 202 is illustrated as having three flanges 256, embodiments are not so limited and can have any number of flanges. The handle 322 may be knurled to facilitate gripping and cylindrical to prevent its descent into the rod 400. In some embodiments, the post 300 further includes an alignment pin hole 324.

In some embodiments, the handle 322 may be profiled in different shapes which include, but are not limited to, a round, flat plate or disc, T-handle, thumb plate, ball, bulb, laterally contoured projections, finger-ring holes, diamond, ribbed finger grip, a rod-like handle, etc. In some embodiments, the shaft of the post 300 may be formed in other non-cruciate shapes, such as geometric shapes like a triangle or diamond, or a simple round or oval profile. Moreover, one or more of the four cruciate crossarms may be added to or removed from the cruciate profile, thus allowing for a variety of shapes which include, but are not limited to, one crossarm projection, two crossarms similar to a dumb-bell shape, three crossarms like a rounded three-leaf clover or a pointed triangular shape, a diamond shape, or multiple rounded or pointed projections as seen in various flower or star-like profiles.

In some embodiments, the breakaway point 320 may be designed to sever either by a snap release, by pulling and/or twisting, or by other physical means, instead of the application of torque discussed above. Additionally, since many of the apparatus's components respond to the body's pH and/or temperature, the breakaway point's chemical properties may be engineered to release within a specific period of time, shortly after deploying the wound plug 200 within the wound.

Figure 4:
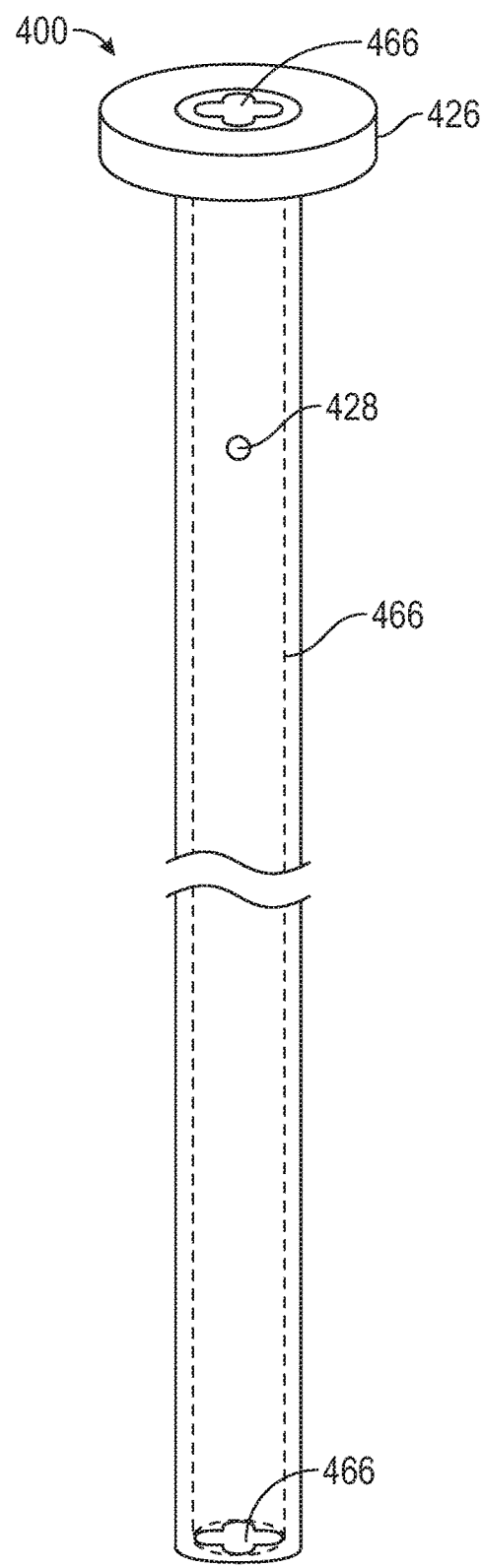
FIG. 4 illustrates a rod according to embodiments of the disclosure.

FIG. 4 illustrates a rod 400 according to embodiments of the disclosure. The rod 400 can include a plate 426 at a second end of the rod, and a first end of the rod can be in contact with the suprafascial rivet head 204 (e.g., the receiving pawl). Prior to deployment, the plate 426 may be positioned midway between the handle 322 of the post 300 and the grips 538 of the shield 500. The rod may further include an alignment pin hole 428. An inner channel 466 of the rod can match a cruciate profile of the post 300, allowing for the vertical movement of the post and the rod without twisting during deployment of each associated rivet head (subfascial rivet head 202 deployed by the post 300, and suprafascial rivet head 204 deployed by the rod 400). Further, the cruciate profile can facilitate fixation of the post 300 above its breakaway point 320, permitting the application of torque to sever the post at the breakaway point.

In some embodiments, the combination of the plate 426 of the rod 400 and the grips 538 of the shield 500 can allow for a syringe-like hold to deploy the suprafascial rivet head 204 and the superior section of the column 206, as described below. In some embodiments, the inner channel 466 of the rod 400 has a non-cruciate shape to match a corresponding non-cruciate shape of the post 300. In some embodiments, the suprafascial rivet head 204 can be a part of the rod 400, separated from the plate 426 by a breakaway point that functions similarly to the breakaway point 320 of the post 300. The breakaway point of the rod can align with the breakaway point of the post after deployment such that a single twisting motion can sever both.

Although the figures illustrate a single shape for the plate 426, variations in shapes, thicknesses, sizes, etc. are contemplated by this disclosure.

FIGS. 5A-5C illustrate a shield 500 according to embodiments of the disclosure. The shield 500 can include a shield cavity 530 and an implant chamber 532 that houses portions of the wound plug 200 prior to deployment. In some embodiments, the shield further includes grips 538 to allow a user to hold the device like a syringe with a comfortable grip for the deployment of the suprafascial rivet head 204 and the column 206. The implant chamber 532 may be profiled in an inverted cup-like configuration. A rim of the implant chamber may be wider than the wound in the fascia, such that the shield 500 can rest on the fascia without entering the wound 744, and so that the contact between the fascia and the rim provides physical feedback to the user indicating that the wound plug is correctly positioned with respect to the depth of the fascia beneath the skin, allowing for use of the apparatus without internal or external direct vision of the wound 744. Further, the rim of the implant chamber may include an insertion lip 534 to facilitate easy insertion of the apparatus beneath a narrow skin incision.

In some embodiments, the shield 500 may further include an alignment pin hole 536. The linear arrangement of the three alignment pin holes in the post 300, the rod 400, and the shield 500 can create a common opening for insertion of an alignment pin 600 to keep the components in place until ready for deployment, as illustrated in FIG. 5C. The alignment pin may be removed once the rim of the implant chamber 532 is centered over the wound in the fascia.

In some embodiments, the insertion lip 534 of the implant chamber 532 may project in shapes including a quarter or half circle, a quarter or half oval, a more pointed design, an encircling band or brim, a ring, or a ridge. One or more additional insertion lips may also be included on the rim of the implant chamber 532.

In some embodiments, a $CO_2$ sensor or pressure gauge may be devised along the rim and/or lip of the implant chamber 532 which can register a visual cue in a window constructed within the wall of the shield 500.

In some embodiments, concentric grooves appearing as screw-like threads or spiral-like grooves may be profiled to the exterior wall of the shield 500. The purpose of these grooves may be to promote an easier insertion of the device within the subcutaneous tunnel of the wound. However, it may be determined that vertically aligned grooves, in contrast to the horizontal grooves, like the screw or spiral-like profiles, may effect easier insertion of the apparatus into the wound.

In some embodiments, some or all of the shield 500 may be profiled in numerous shapes, sizes, thicknesses, etc. For example, the grips 538 may be profiled in any geometric shape for designing the laterally oriented projections or rings, and any number of grips are contemplated.

Method of Deployment

Figure 6A:
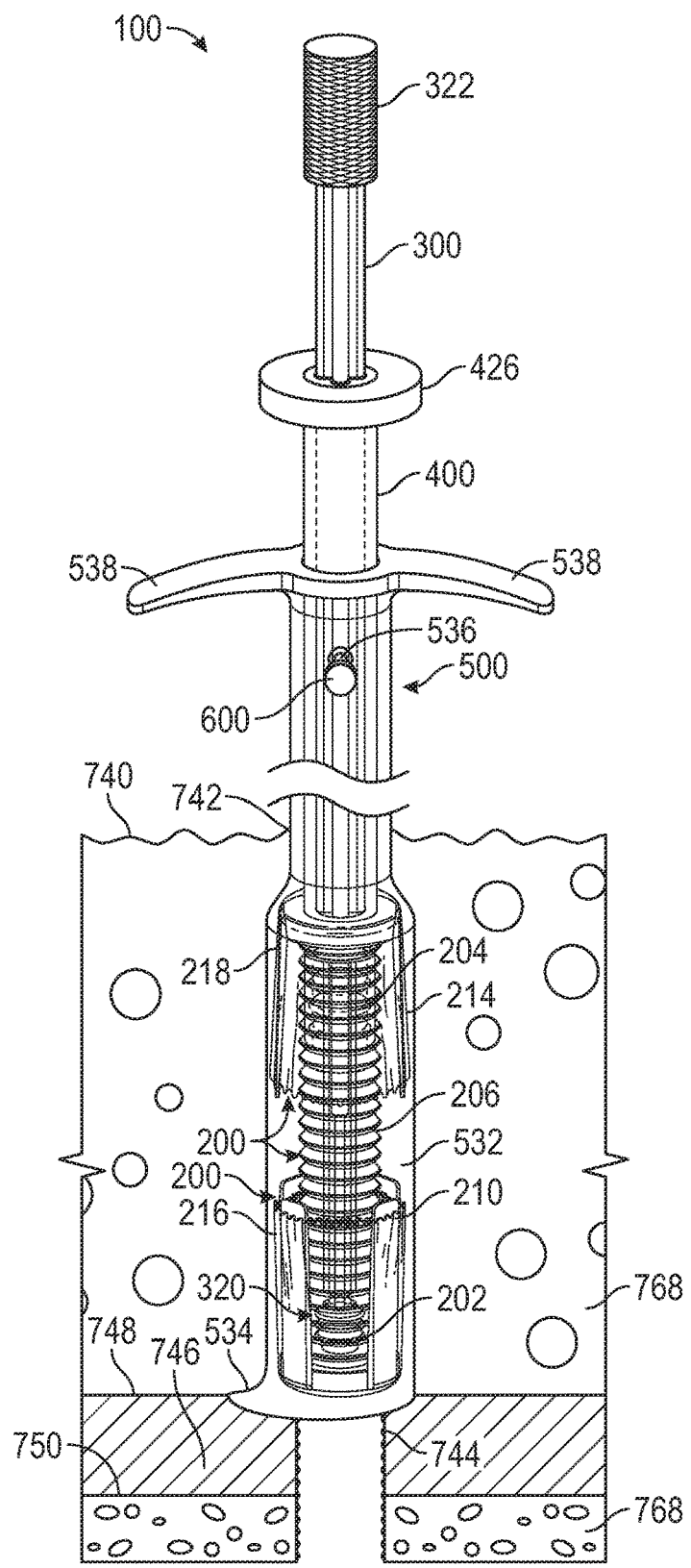
FIGS. 6A-6D illustrate the apparatus during stages of deployment of the wound plug according to embodiments of the disclosure.
Figure 6B:
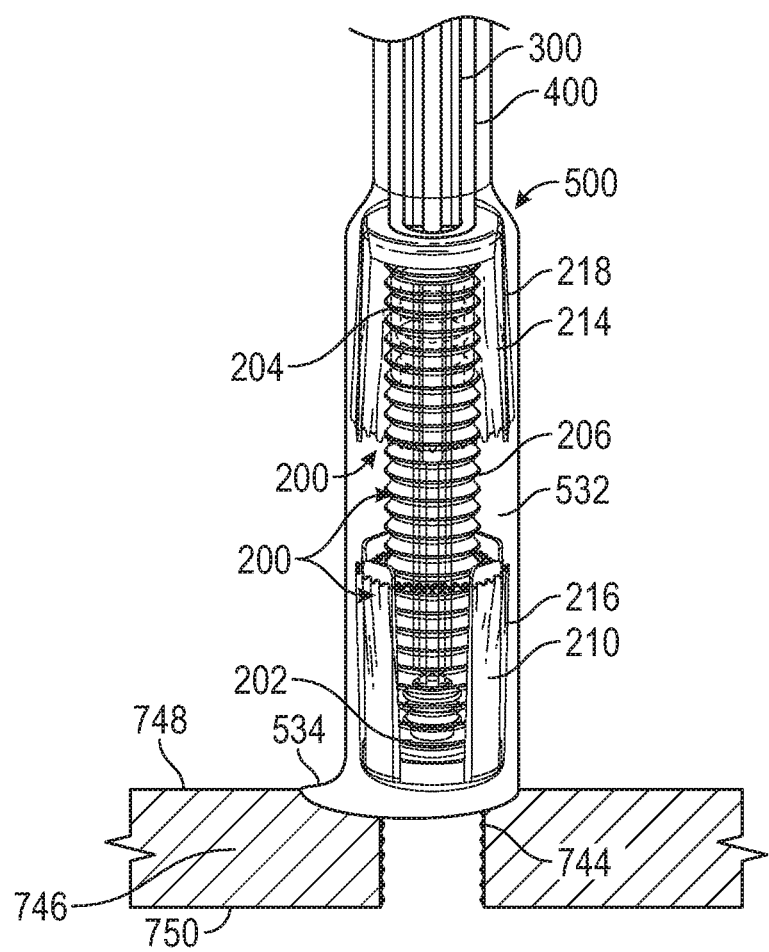
Figure 6C:
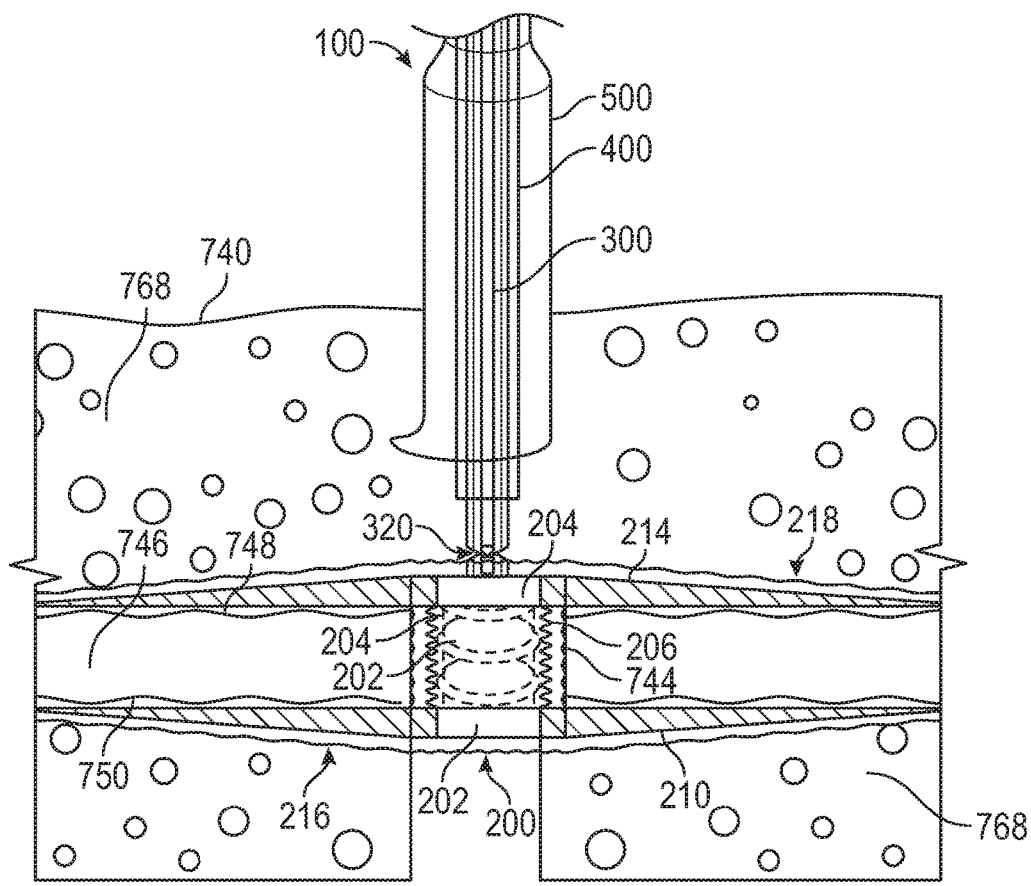
Figure 6D:
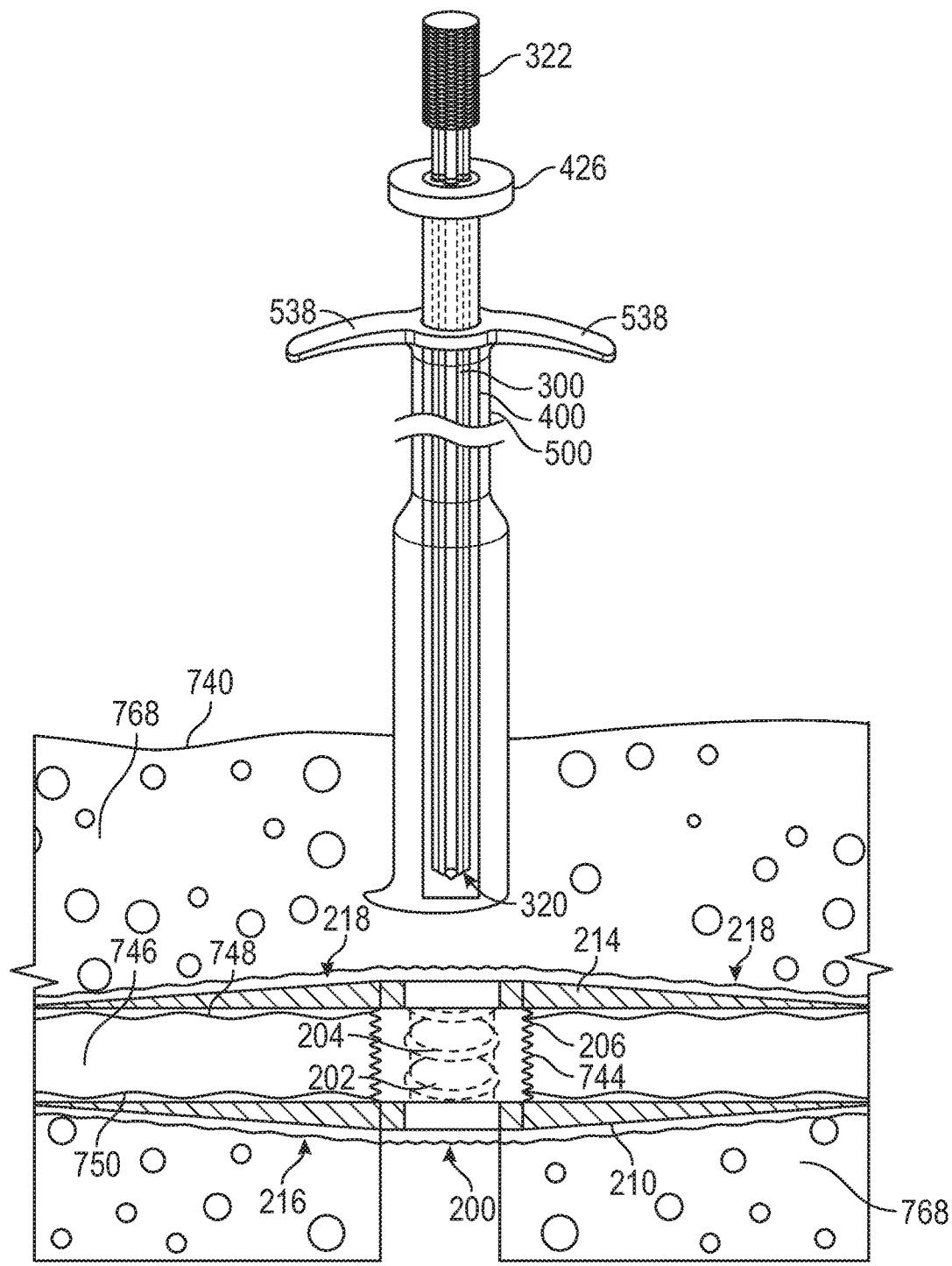
Figure 7:
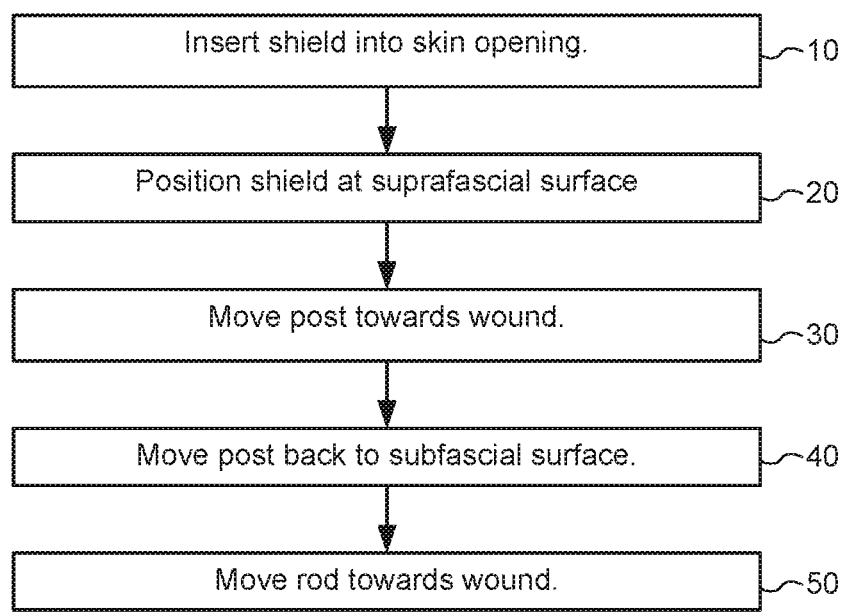
FIG. 7 is a block diagram of a method for deploying a wound plug according to embodiments of the disclosure.

FIGS. 6A-6D illustrate the apparatus 100 during stages of deployment of the wound plug 200, and FIG. 7 is a block diagram of a method for deploying a wound plug according to embodiments of the disclosure.

The shield 500 may be inserted (10) into a skin opening 742 in the skin 740. The shield's implant chamber 532 may be slightly larger than the skin opening 742, so holding the apparatus at a 45° angle may allow the apparatus to slip easily beneath the skin incision without extension of the wound or the need for skin retraction.

The shield may be positioned (20) such that the rim of the implant chamber 532 is in contact with a suprafascial surface 748 of fascia 746 surrounding a wound 744 in the fascia, as illustrated in FIGS. 6A-6B. In some embodiments, the rim of the implant chamber may be wider than the wound in the fascia, such that the shield can rest on the fascia 746 without entering the wound 744, and allowing for use of the apparatus without internal or external direct vision of the wound in the fascia. Further, the contact between the fascia and the rim may provide physical feedback to the user that the wound plug is correctly positioned with respect to the depth of the fascia 746 beneath the skin 740.

In some embodiments, the alignment pin 600 may be removed from the alignment pin holes 324, 428, and 536 of the post 300, the rod 400, and the shield 500, respectively.

The post 300 may be moved (30) towards the wound 744 (e.g., by gripping and moving the handle 322 of the post) such that a subfascial extension 208 coupled to the subfascial rivet head 202 (e.g., engaging ratchet) at the first end of the post passes through the wound. The subfascial rivet head 202, the subfascial biohybrid scaffold 216, and an inferior portion of the column 206 may thereby pass into the native tissues 768 of the pre-peritoneal space.

After the subfascial extension 208 passes through the wound 744, the post 300 may be moved (40) such that the subfascial extension is in contact with a subfascial surface 750 around the wound 744 (e.g., by gripping and pulling the handle 322 of the post until resistance is felt when the subfascial extension comes into contact with the subfascial surface). The subfascial biohybrid scaffold 216 and corresponding subfascial plurality of stays 210 of the subfascial extension may be fully radially expanded at this point below the fascial defect within the pre-peritoneal space. Further, the inferior portion of the column 206 containing a portion of the subfascial rivet head 202 may positioned within the wound.

The rod 400 may be moved (50) toward the wound 744 (e.g., by holding the handle 322 of the post 300 in a stationary position with one hand, and with the opposite hand pushing together in a syringe-like manner the grips 538 of the shield 500 and the plate 426 of the rod). As a result of this motion, the receiving pawl 204 may be pushed by the rod towards the engaging ratchet 202, the engaging ratchet may interlock within the receiving pawl, the compressible column 206 may be compressed within the wound, and a suprafascial extension 212 (e.g., including a plurality of stays 214) coupled to the receiving pawl may be in contact with a suprafascial surface 748 around the wound 744, as illustrated in FIG. 6C. The interlocking of the receiving pawl and the engaging ratchet within the inner channel 260 of the column 206 may cause the mechanical compression of the column within the wound 744, as illustrated in FIG. 6D. Further, the suprafascial biohybrid scaffold 218 and corresponding suprafascial plurality of stays 214 of the suprafascial extension may be fully radially expanded at this point. As a further result of this motion, portions of the wound plug 200 may be driven out of the implant chamber 532, and the implant chamber may be lifted off the suprafascial surface 748 to allow for unrestricted clearance of the suprafascial rivet head 204 and the column 206 into the wound 744. Further, three consecutive clicks may be heard and felt by a user to indicate that the wound plug is fully deployed.

In some embodiments, the post 300 may be twisted to break the post at the breakaway point 320 such that the engaging ratchet is separated from the post, as illustrated in FIG. 6D. In some embodiments, both an outer profile of the post and an inner profile of the rod cavity have a cruciate shape, such that post is prevented from rotating within the rod cavity (e.g., to facilitate the application of torque to a breakaway point of the post when the rod is twisted).

In some embodiments, any or all components of the apparatus may be assembled within any disposable or non-disposable surgical gun or applier, and these may be designed with automatic reloads of the wound plug, either within the apparatus or applied separately to it, for sequential and repetitive deployment.

In some embodiments, the wound plug 200 may afford stabilization and/or healing of any type of penetrating wound caused by traumatically impaling the fascia anywhere on the body. The wound plug may appropriately address various types of hernias within the abdominal wall. The wound plug's postoperative antimicrobial benefits may be feasible for the primary closure of fistulated tracks or other types of reoccurring infected wounds. The wound plug's antimicrobial and anesthetic advantages, as well as its ability for completely healing these chronic wounds, may eliminate lengthy secondary or tertiary healing attempts, which often succumb to re-infection and reoccurrence. By application of the apparatus 100, the wound plug 200 may be considered possible for closing the abdominal fascial defect of a stoma (i.e., colostomy) following surgical re-anastomosis of the bowel. The wound plug may close any fascial defect following the removal of any large drainage tube, surgical tube, or port that is at high risk for herniation or poor wound healing, in general.

In some embodiments, the wound plug 200 may be made to address any length or shape of fascial incision anywhere on the body, with or without the incorporation of sutures for reinforcement. For example, the wound plug may be in a more rectangular and linear profile, thus allowing for its repetitive and sequential application along the fascial incision line. Fascial incisions may include, but are not limited to, any region of the abdomen (i.e., midline or transverse laparotomy incisions), any location on the extremities (i.e., incisions for repairing fractured bones or joint replacement arthroplasties), posterior or flank regions of the torso (i.e., spinal or kidney incisions), or fascial planes covering the anterior, lateral, or posterior areas of the chest wall (i.e., video assisted open thoracostomy port-site wounds or thoracostomy incisions).

In some embodiments, the apparatus 100 may be designed to incorporate a fiber optic cable with an optical lens to allow for direct visualization of the subcutaneous tunnel and anterior abdominal fascia during its insertion and deployment within the wound. Although embodiments of the disclosure are described without requirement of a pneumoperitoneum, intra-abdominal telescopic lens, or any other instrumentation, the apparatus may be used in conjunction with such devices.

In some embodiments, the apparatus 100 may further include one or more elements to enhance light (or visual), auditory, or palpatory sensations when the rim of the shield 500 reaches the wound in the fascia 746 and/or as confirmation of accurate completion of other various steps during deployment. For example, a rim or lip 534 of the shield 500 may further include a touch-sensitive surface (mechanical, capacitive, and/or resistive, among other possibilities) to confirm that the rim has reached the wound in the fascia. Further, an audible sound may confirm the subfascial rivet head's placement below the fascia, and a light sensor may confirm engagement of the suprafascial and subfascial rivet heads (or any combination of sensor feedback).

In some embodiments, the apparatus 100 may further include a button-type retaining pin (either spring or manually designed) which, by virtue of its configuration, could function to lock and unlock the post 300. Once this retaining pin is pushed in to become flush with an external wall of the shield 500, a grooved configuration would release only the post 300, allowing its downward movement for deploying the subfascial rivet head 202.

In this embodiment, the alignment pin 600 can interlock the actuator rod 400 and shield 500 together prior to their deployment. After a user pushes the button of the retaining pin forward (toward the shield 500), the post 300 is released and may slide down as previously described. When the user pulls the post 300 upward in order to palpate the subfascial tissue 750, the retaining pin of the post may be pulled back toward the operator, out of its hole, until it engages the post in its locked configuration. Following the aforementioned activity of the post's retaining pin, the alignment pin 600 can be pulled out to release the rod 400 and the shield 500 for their deployment of the suprafascial rivet head 204. Naturally, with regards to this alternative, the profiles of the rod 400 and shield 500 would need to incorporate some sort of detent/horizontal slots or grooves to allow for their deployment activities over and alongside the presence of this stationary retaining pin. Such a configuration may allow for a more controlled and sequential release of the elements incorporated within the apparatus 100, freeing the user from needing to hold the post 300 stationary during the activation of the rod 400 and shield 500.

Additional Embodiments

Figures 8A, 8B:
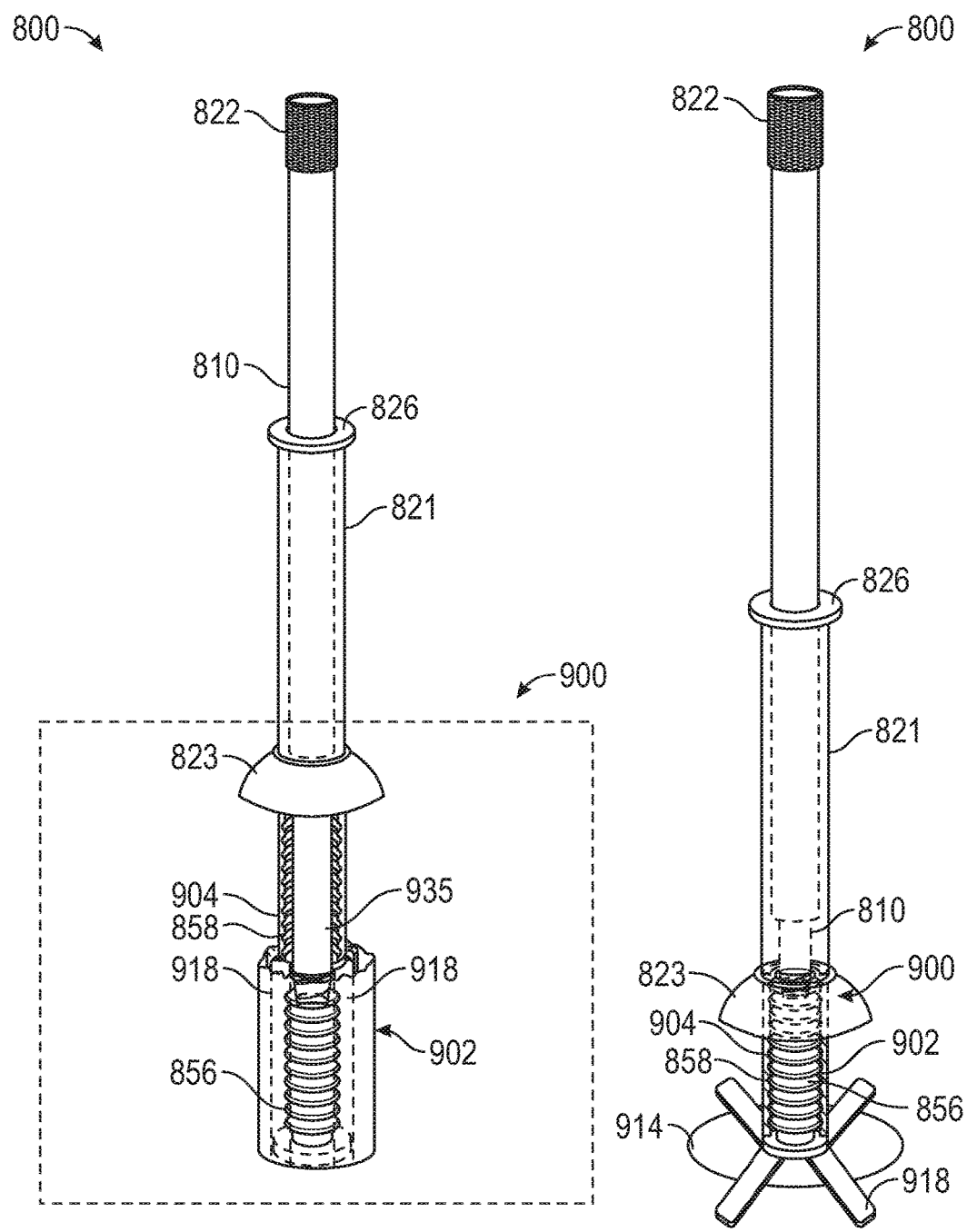
FIGS. 8A-8B illustrate a wound closure apparatus including wound plug according to embodiments of the disclosure.

FIG. 8A illustrates a wound closure apparatus 800 and wound plug 900 in an assembled configuration according to embodiments of the disclosure. The apparatus 800 may be a self-contained device for delivery and deployment of a tissue engineered wound plug 900 that can secure fascial closure of wounds. The wounds can be laparoscopic port-site wounds, fistulas, sinus tract wounds, traumatic wounds or the like. FIG. 8B illustrates a wound closure apparatus 800 and wound plug 900 in a deployed configuration according to embodiments of the disclosure.

Figure 9A:
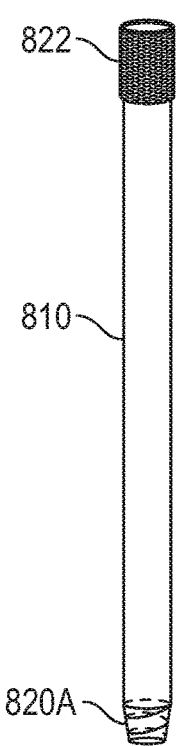
FIG. 9A illustrates a post according to embodiments of the disclosure.

The apparatus 800 may include a post 810 and a rod 821 for delivery and deployment of the wound plug 900. In some embodiments, the apparatus 800 may exclude a shield and an alignment pin (discussed above). FIG. 9A illustrates a post according to embodiments of the disclosure. The post 810 may include a coupling attachment 820A at a first end of the post and a handle 822 disposed at a second end. The coupling attachment 820A may be configured to temporarily attach to the wound plug 900. The handle 822 of the post 810 may be knurled and cylindrical. In some embodiments, the handle 822 may be profiled in different shapes which include, but are not limited to, a round, flat plate or disc, T-handle, thumb plate, ball, bulb, laterally contoured projections, finger-ring holes, diamond, ribbed finger grip, a rod-like handle and the like.

In some embodiments, the shaft of the post 810 may be circular and smooth. In some embodiments, the post may be formed in other non-cruciate shapes, such as geometric shapes like a triangle, diamond, a simple round or oval profile, a semi-circle shape, etc. In some embodiments, the post may be formed in a cruciate shape. Moreover, one or more of the four cruciate cross-arms may be added to or removed from the cruciate profile, thus allowing for a variety of shapes which include, but are not limited to, one cross-arm projection, two cross-arms similar to a dumb-bell shape, three cross-arms like a rounded three-leaf clover or a pointed triangular shape, a diamond shape, or multiple rounded or pointed projections as seen in various flower or star-like profiles. In some embodiments, the post 810 may exclude an alignment pinhole.

Figure 9B:
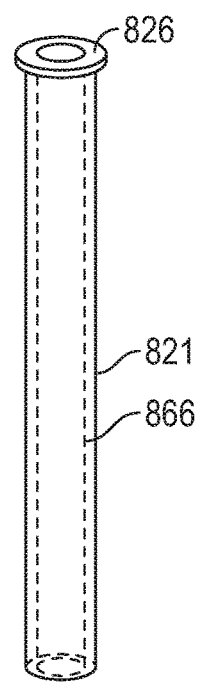
FIG. 9B illustrates a rod according to embodiments of the disclosure.

FIG. 9B illustrates a rod 821 according to embodiments of the present disclosure. The rod 821 may have a rod cavity 866 through which the post 810 is positioned. Thus, the post 810 and the rod 821 can form an apparatus 800 for delivery and deployment of the wound plug 900. In an assembled configuration, a first end of the rod 821 may be in contact with a first end of the wound plug 900 as shown in FIG. 8A. A second end of the rod 821 may include a plate 826. The plate 826 may act as a handle for the rod, thereby allowing a user to more easily manipulate the rod 821.

Figure 9C:
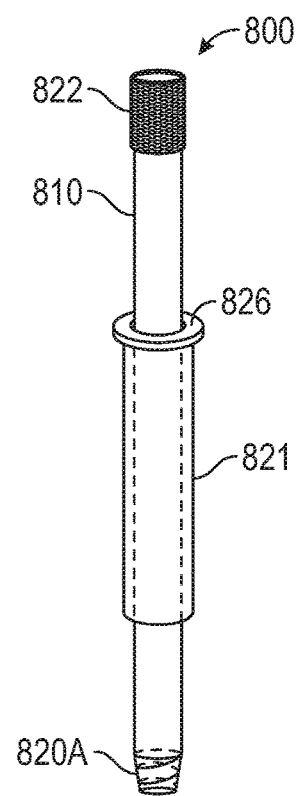
FIG. 9C illustrates a wound closure apparatus according to embodiments of the disclosure.

Referring to FIG. 9C, the post 810 and the rod 821 may reside at different radial levels in the apparatus 800. The post 810 may serve as an axis that is vertical and innermost to which the components of the apparatus 800 and wound plug 900 may be collectively aligned and integrated for deployment. For example, the alignment of the cannulated components of the rod 821 and wound plug 900, e.g., suprafascial rivet head 204, can create a common passageway through which portions of the post 810 can move for deployment of the wound plug 900.

The post 810 may be located in the core of the apparatus 800 and may be the longest of the components, with its handle 822 rising higher than the other components. Referring again to FIG. 8A, in some embodiments, the plate 826 of the rod 821 may be positioned at one end approximately midway between the handle 822 and the subfascial rivet head 902 when the apparatus 800 is coupled to the wound plug 900, i.e., when coupling attachment 820A of the post 810 is coupled to the breakaway connection 820B of subfascial rivet head 902 described in further detail with respect to FIGS. 11A-11C.

The shaft of the rod 821 may be non-cruciate and smooth to correspond to the shaft of the post 810. For example, the interior of the rod 821 may be smooth and configured to receive the post 810. If the shaft of the post 810 has a cruciate shape, the shaft of the rod 821 would similarly have a cruciate shape. The rod cavity 866 may facilitate the vertical stability and movement of the post 810 before, during, and after deployment of the wound plug 900. In some embodiments, the rod 821 may not include an alignment pinhole.

In some embodiments, the post 810, the rod 821, or both may include rigid materials comprising elements (e.g., the elements that will not be implanted within the body) that may be fabricated from non-critical, bio-safe materials. In some embodiments, portions of the post 810, rod 821, or both may include a flexible or semi-flexible material that can allow the flexible portions to follow the course of a tract, such as a fistulated tract.

Figure 10A:
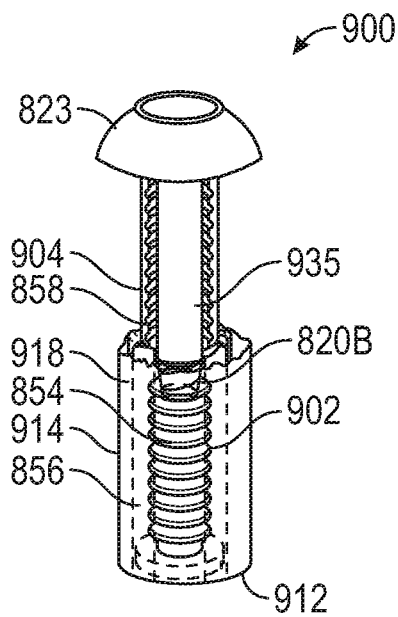
FIG. 10A illustrates a wound plug according to embodiments of the disclosure.

FIG. 10A illustrates a wound plug 900 in according to embodiments of the present disclosure. In some embodiments, the wound plug 900 may be one piece that includes a first portion 904 molded to a second portion 902. The first portion 904 may extend from a first, proximate end of the wound plug to a breakaway connection 920B. In some embodiments, first portion 904 may correspond to a suprafascial rivet head. The second portion may extend from a second, distal end or base 912 of the wound plug to the breakaway connection 920B. The second portion may include the breakaway connection 920B. In some embodiments, the second portion 902 may correspond to a subfascial rivet head. According to some embodiments, the wound plug 900 may not include a compressible column.

Figure 10B:
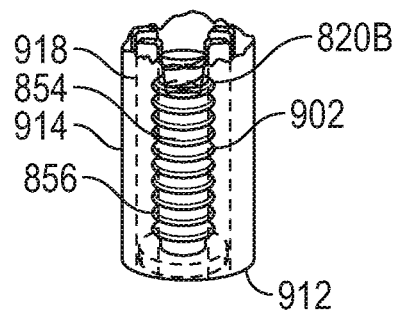
FIG. 10B illustrates a subfasical rivet head according to embodiments of the disclosure.

FIG. 10B is a second portion or subfascial rivet head 902 of the wound plug 900 according to embodiments of the present disclosure. The subfascial rivet head 902 may include a body 854 having a base 912 located at the second end of the wound plug opposite a breakaway connection 820B. The breakaway connection 820B is configured to receive the coupling attachment 820A of the post 810. In some embodiments, the body 854 of the subfascial rivet head 902 may include a plurality of annular flanges 856. The plurality of annular flanges 856 may extend from the base 812 to the breakaway connection 820B. The plurality of annular flanges 856 may allow the subfascial rivet head 902 to act as a ratchet when engaging with the suprafascial rivet head 904. In other words, the engagement of annular flanges 856 and 858 permit movement in one direction.

The subfascial rivet head 902 may also include at least one stay 918 connected to the subfascial rivet head 902 at the base 812. As illustrated in FIG. 10B, the subfascial rivet head 902 includes a plurality of stays 918. The plurality of stays 918 may be fabricated using shape memory properties, allowing for multiple different configurations during the implant's surgical application. Prior to deployment, the plurality of stays 918 may project at 90° angles from an outer perimeter of the subfascial rivet head 902. Once the rivet head 902 is deployed, the shape memory properties of the plurality of stays 918 can be affected by the body's temperature and/or pH relative to a pre-determined time interval also inherent in their chemical properties. These physical and biological properties can cause each stay 918 to automatically deploy into a full radial expansion.

The subfascial rivet head 902 may include a biohybrid scaffold 914. For example, in some embodiments, the biohybrid scaffold may be fully perforated with micro-perorations to allow for the native tissue integration, takeover, and eventual destruction of the scaffold in order for natural materials and tissue to fill the void in the wound. In some embodiments, the biohybrid scaffold 914 may cover and embed portions of the subfascial rivet head 902. In some embodiments, the biohybrid scaffold 914 may cover the stay or plurality of stays 918.

FIGS. 10C-10F illustrate embodiments of the suprafascial rivet head 904 according to embodiments of the present disclosure. The suprafascial rivet head 904 may comprise a hollow receiving pawl configured to engage with an engaging ratchet of the subfascial rivet head 902. For example, the receiving pawl may include a number of reciprocal annular grooves 858 configured within its interior that correspond to a number of flanges 856 on the exterior of the subfasical rivet head 902. Further, the suprafascial rivet head 904 may be configured with a channel 935 to allow the post 810 to pass through its hollow core. In some embodiments, engagement of the subfascial and the suprafascial rivet heads 902 and 904, respectively, may be confirmed by audible clicks synchronized with tactile sensations.

Figure 10C:
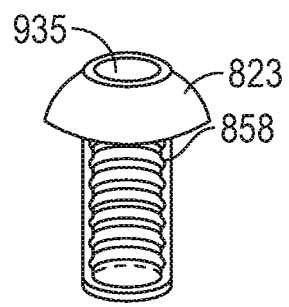
FIGS. 10C-10F illustrates a suprafascial rivet head according to embodiments of the disclosure.

The suprafascial rivet head 204 may also include at least one suprafascial extension disposed on a first end of the wound plug. The extension may abut the first end of the rod 821 when the apparatus 800 and wound plug 900 are in an assembled configuration, e.g., shown in FIGS. 8A-8B. Referring specifically to FIG. 10C, the shape of the suprafascial extension is a cup 823. The suprafascial extension cup 823 may be any size, shape, thickness, or configuration. For example, the suprafascial extension cup 823 may project at an angle (e.g. 80 or 90 degrees, etc.) from an outer perimeter of the suprafascial rivet head 904.

Like the plurality of stays 918 of the subfascial rivet head 902, the suprafascial extension cup 823 may be developed from either biological or chemical polymers. For example, the suprafascial extension cup 823 may be electrospun or dip coated with an absorbable chemical polymer to enhance its full radial expansion on the anterior abdominal fascia. Once the suprafascial rivet head 904 is deployed, the shape memory properties of the suprafascial extension cup 823 may be affected by the body's temperature and/or pH relative to a pre-determined time interval also inherent in their chemical properties. These physical and biological properties may cause the sides of the suprafascial extension cup 823 to automatically deploy into a full radial expansion. In some embodiments, the suprafascial extension cup may serve as a biohybrid scaffold. For example, the suprafascial extension cup 823 may include micro-perforations to allow for native tissue ingrowth and takeover.

Figure 10D:
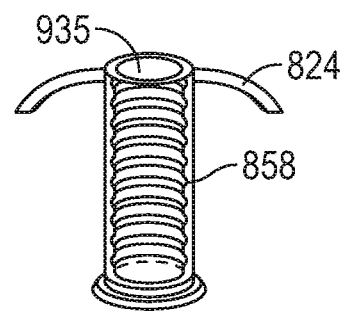
Figure 10E:
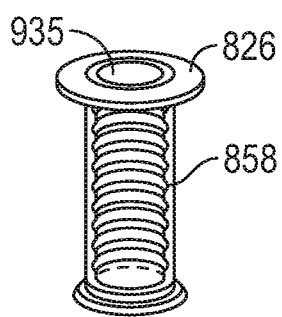
Figure 10F:
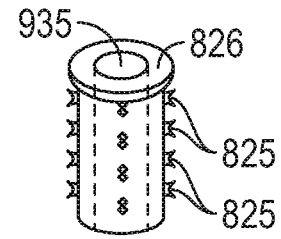

Referring to FIG. 10D, the suprafascial rivet head 904 may include a suprafascial extension in the shape of stays 824. In some embodiments, the suprafascial rivet head 904 may include one large suprafascial stay-extension 824 or multiple suprafascial stay-extensions 824 (not shown). In some embodiments, as depicted in FIGS. 10E and 10F, the suprafascial rivet head 904 may include a suprafascial extension plate 826. The variations of the suprafascial extensions in FIGS. 10D-10F may have the same physical properties and chemical make-up as described with respect to suprafascial extension cup 823.

In some embodiments, as seen in FIG. 10F, an outer surface of the suprafascial rivet head 904 may include a plurality of external polymer barbs 825. External barbs 825 may anchor the suprafascial rivet head 904 to the native tissues of the wound. Specifically, when the wound plug 900 is inserted into a wound and the post 810 is removed, the barbs 825 may catch the tissue of the wound, thereby anchoring the deployed wound plug in the wound. The barbs 825 may allow the wound plug 900 to be embedded in wounds in a variety of tissue types. For example, the barbs 825 can fasten the suprafascial rivet head 904 within the space of the wound and even into the blind-end of the sinus tract.

In some examples, the barbs 825 can be circumferentially oriented features that project from the interior of the wound plug 900. In some embodiments, the barbs 825 can surround the subfascial rivet head 904 of the wound plug 900 in a spiral orientation (not shown). In some embodiments, the barbs 825 may be unidirectional, having features pointing in the same directions such as towards the second end of the wound plug 900. In some embodiments, as illustrated in FIG. 10F, the barbs 825 may be positioned bi-directional or multi-directional.

The wound plug 900 (including the barbs 825) may be composed of natural polymers or copolymers like chitosan, gelatin, alginate, collagen and/or other wound healing promoters; as well as synthetic polymers or copolymers such as PGA, PLA, PDO, PCL, PLLA, or synthetic copolymers like PLGA. The possibilities for such fabrication techniques may include but are not limited to polymeric blends, dip coating, adhesive layering, copolymerization, grafting, homogeneous mixtures, and/or electrospinning for creating a biosynthetic composite material. In some embodiments, the wound plug can comprise one or more surgical dressing materials such as gauze, silicon, rubber, etc.

Figure 11C:
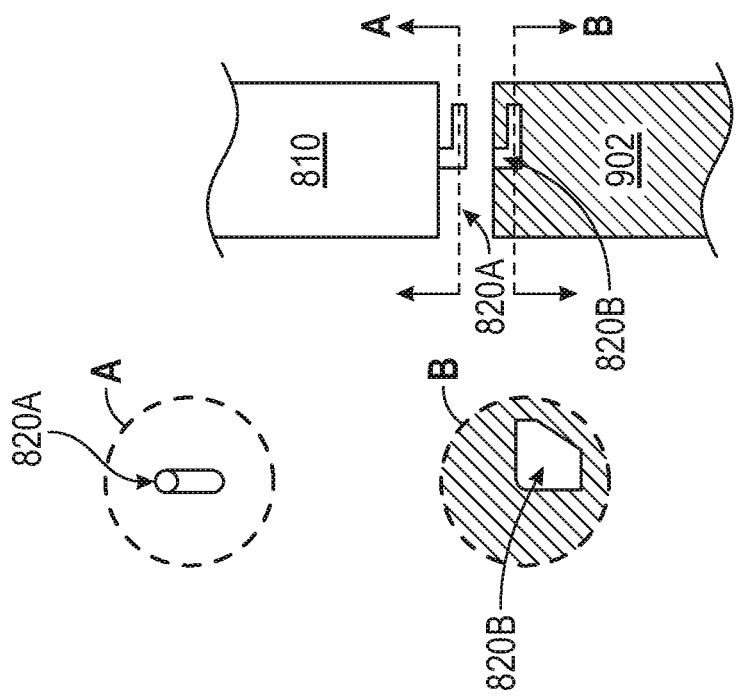
FIGS. 11A-11C illustrate a coupling mechanism according to embodiments of the disclosure.
Figure 11B:
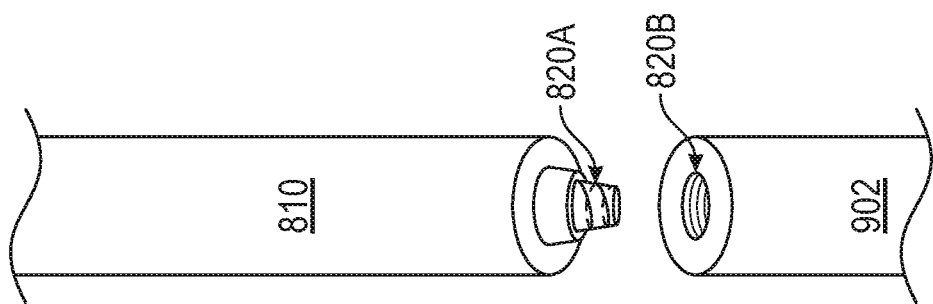
Figure 11A:
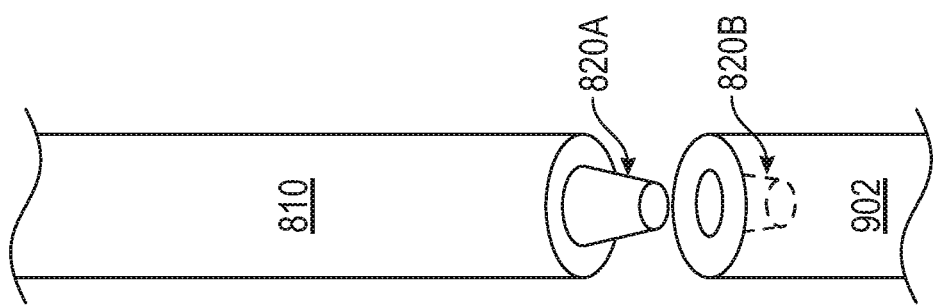

FIGS. 11A-11C illustrate a number of variations of the coupling attachment 820A and the breakaway connection 820B used to couple the apparatus 800 with the wound plug 900. Typically, the coupling attachment 820A will be a male (i.e., protruding) component. This may allow the post 810 to more easily navigate the cannulate cavities of rod 821 and suprafascial rivet head 904 to mate with the corresponding female breakaway connection 820B. In some embodiments, the connection between coupling attachment 820A and the breakaway connection 820B may provide vertical stability and strength to the apparatus 800 and wound plug 900 assembly, thereby allowing the device to resist compression or elongation during insertion and deployment.

Referring to FIG. 11A, the coupling attachment 820A and the breakaway connection 820B may be configured to have a press-fit. In the press-fit configuration, the dimensions of the coupling attachment 820A will be configured to overlap with the dimensions of the breakaway connection 820B. In this manner, an interference fit results when the post 810 and the subfascial rivet head 902 of the wound plug 900 are pressed together.

FIG. 11B illustrates a luer-lock configuration. In the luer-lock configuration, the post 810 is advanced through the interior cannula 866 of the suprafasical rivet head 904 until the coupling attachment 820A abuts the breakaway connection 820B. The post 810 may then be rotated in order to have the coupling attachment 820A rotate and lock into the breakaway connection 820B. In other embodiments, the post 810 may be further pressed in order to have the coupling attachment 820A click and lock into the breakaway connection 820B.

FIG. 11C illustrates a cam-lock configuration. In the cam-lock configuration, the coupling attachment 820A may include a cam protrusion. The cam protrusion 820A may be positioned in a corresponding keyhole shaped breakaway connection 820B disposed on the subfascial rivet head 902. Once in the keyhole shaped breakaway connection 820B, the cam protrusion can be rotated to lock the post 810 of the apparatus 800 to the wound plug 900. Although a specific cam-lock and keyhole shape is illustrated in FIG. 11D, for example, at cross-sections A and B, one skilled in the art will understand that a variety of cam-lock and keyhole shapes may be used without departing from the scope of this disclosure.

According to embodiments of this disclosure, despite the particular variant (pressfit, luer-lock, or cam-lock), the post 810 may be rotated to release or unscrew and detach coupling attachment 820A from the breakaway connection 820B. By this described detachment, the non-critical elements of the apparatus 800 (e.g., the post 810 and rod 821) are separated from the wound plug 900, and removed from the wound.

In some embodiments, the temporary attachment between the coupling attachment 820A and the breakaway connection 820B may be designed to be pre-attached and permanently severed by a physical means such as a ballpoint pin snap release (the button would be constructed in the handle 822), pull, twist, or the like, instead of the application as discussed previously above. Additionally, since many components of the apparatus 800 may respond to the body's pH and/or temperature, the breakaway connection 820B of the subfascial rivet head 902 may be fabricated with chemical properties that are engineered to release within a specific period of time shortly after deploying the wound plug.

The assembly of the apparatus 800 and wound plug 900 may be completed at a sterile operating room table prior to inserting and deploying it within a port site wound, or fistula/sinus track. Specifically, the post 810 may be positioned within the cavity 866 of the rod 821. The post 810 may extend through the rod cavity 866 and into the wound plug 900, where connecting attachment 820A can be coupled to the breakaway connection 820B. In some embodiments, a tactile sensation or audible response may indicate that the apparatus 800 and wound plug 900 are coupled in the assembled configuration.

Figure 12A:
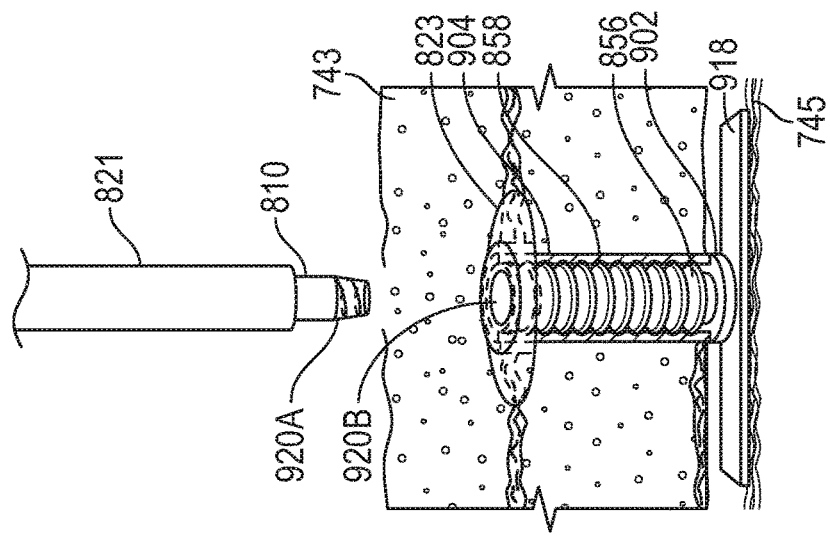
FIGS. 12A-12C illustrates a wound closure apparatus during stages of deployment of the wound plug according to embodiments of the disclosure.
Figure 12B:
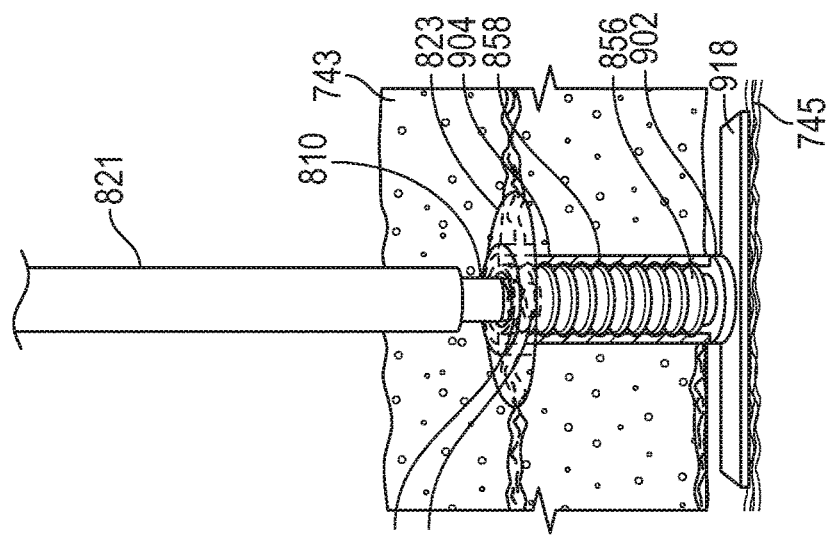
Figure 12C:
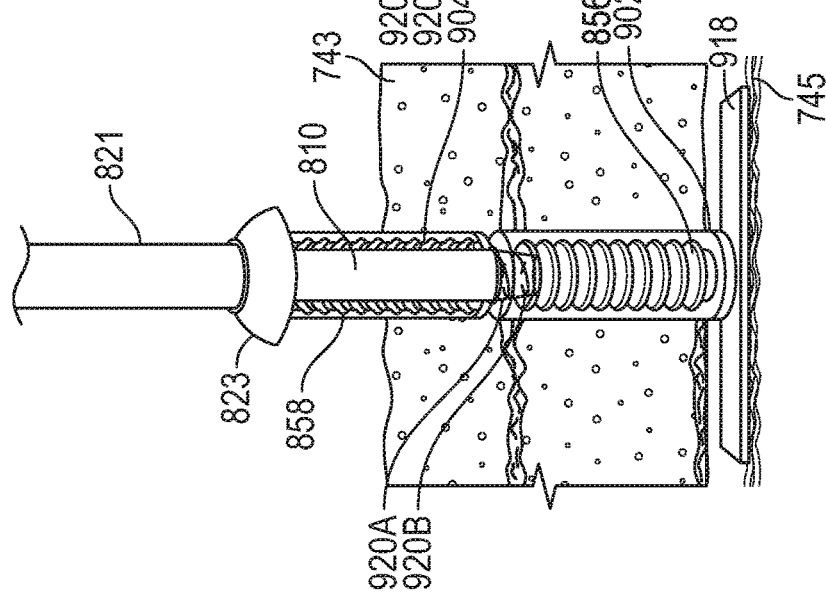
Figure 13:
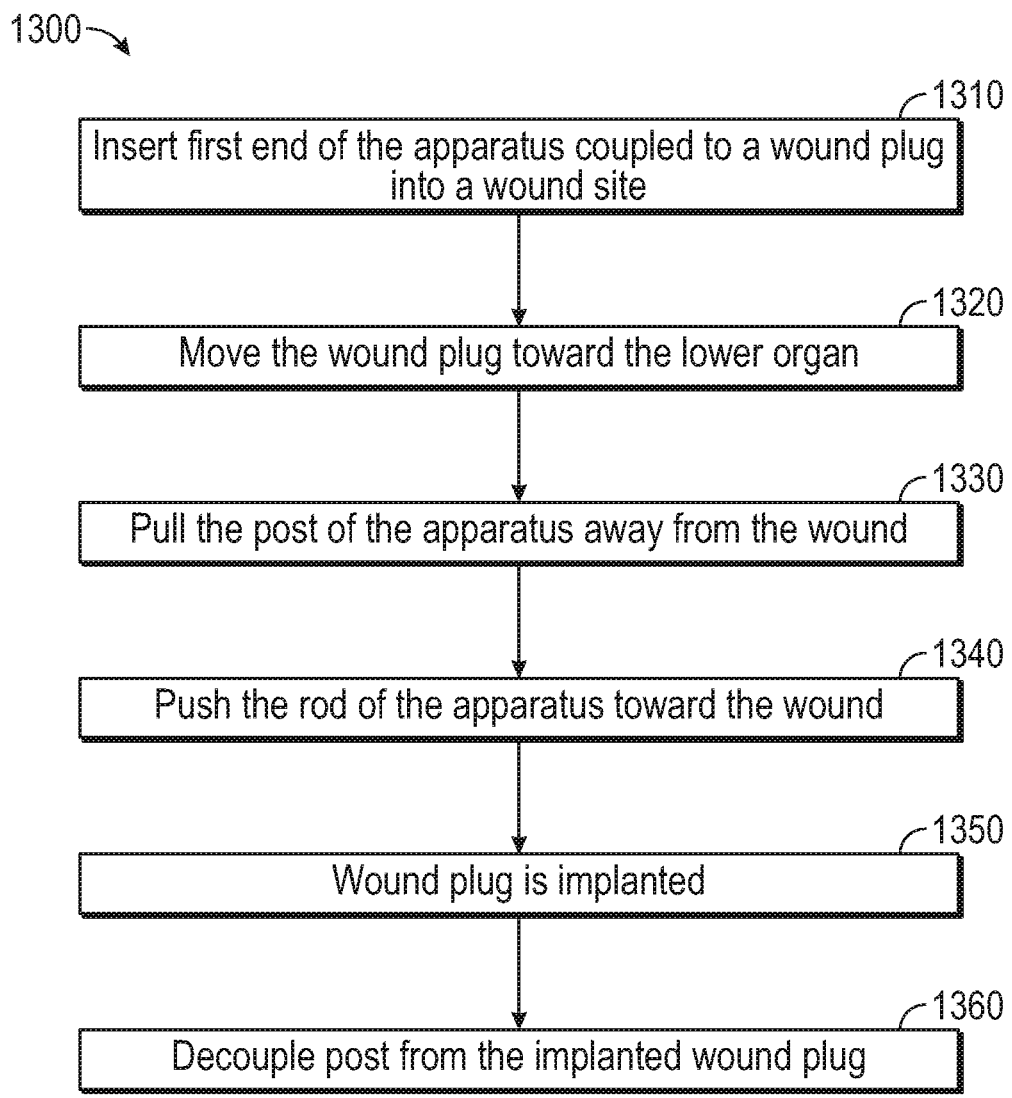
FIG. 13 is a flowchart of a method of deploying a wound plug according to embodiments of the disclosure.

Once the apparatus 800 and wound plug are assembled, e.g., as shown in FIG. 8, the apparatus may be used to deploy the wound plug 900 in a wound site. FIGS. 12A-12C illustrates the deployment of a wound plug according to embodiments of the disclosure. FIG. 13 is a block diagram of a method for deploying a wound plug according to embodiments of the disclosure. The first end of the apparatus 800 can be inserted (step 1310) into a wound site, e.g., near upper organ 743. As shown in FIG. 12A, the wound plug 900 may be moved (step 1320) to a position above lower organ 745. The moving may be performed by gripping the handle (not shown) of the post and maneuvering the wound plug 900 through the wound hole such that the plurality of stays 918 and the biohybrid scaffold located at the first end the wound plug 900 can open in full radial expansion, thereby occluding the wound hole above lower organ 745.

The wound plug may be deployed or implanted in the wound by raising (step 1330) the post 810 up and away from the wound site. For example, the handle 822 may be raised upward. This movement may cause the subfascial rivet head 902 and suprafascial rivet head 904 to interlock. Specifically, the subfascial rivet head 902 coupled to the connecting attachment 820A may move upward such that the plurality of flanges 856 disposed on the subfascial rivet head engage with the plurality of ridges 858 disposed on the suprafascial rivet head 904. The interlocking of the plurality of flanges 856 and the plurality of ridges 858 may create a tactile sensation, which notifies a user that the subfascial rivet head 902 and suprafascial rivet head 904 are interlocked. In some embodiments there will also be an audio cue that accompanies the tactile sensation. In some embodiments the engagement of the plurality of flanges 856 the plurality of ridges 858 acts as a ratchet mechanism, permitting relative movement of the subfascial rivet head 902 in a single direction.

Once the subfascial rivet head 902 and suprafascial rivet head 904 are engaged, the user may push (step 1340) the rod 821 downward toward the wound site to expand the suprafascial extension, e.g., cup 823, radially outward below upper organ 743. In some embodiments, the user may push the plate 826 downward while simultaneously pulling the handle 822 upward to ensure proper placement of the wound plug 900 during deployment. Thus, the wound plug is fully implanted (1350) as shown in FIG. 12B.

Once the wound plug is implanted, the apparatus 800 may be decoupled (Step 1360) from the wound plug 900 as shown in FIG. 12C. For example, the user may rotate and pull the post 810 in order to decouple the connecting attachment 820A from the breakaway connection 820B. The detachment of the connecting attachment 820A from the breakaway connection 820B may be confirmed by a tactile sensation and in some embodiments, audible clicks.

Once the post 810 and the rod 821 are separated from the wound plug and removed from the wound, their byproducts may be safely discarded as environmentally friendly, non-toxic wastes. In some embodiments, the post 810 and the rod 821 can be reloaded and reused multiple times. For example, the apparatus 800 with the same post 810 and rod 821 may be reassembled to be reused with a second wound plug 900. In some embodiments, the apparatus 800 may be cleaned and sterilized prior to assembling the apparatus 800 with the second wound plug 900. Alternatively, the same post 810 and a different rod, or a different post 810 and the same rod 821, may be used for the second wound plug 900.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. An apparatus for deploying a wound plug, the apparatus comprising:
   a post having a first end and a second end, wherein the first end of the post includes a coupling attachment;
   a rod having a first end, a second end, and a rod cavity, the rod cavity extending from the first end of the rod to the second end of the rod; and
   a wound plug having a first end, a second end, and a breakaway connection, the breakaway connection located between the first end of the wound plug and the second end of the wound plug, wherein the wound plug further includes:
   a distal portion having a plurality of annular flanges located between the second end of the wound plug and the breakaway connection; and
   a proximate portion having a plurality of annular grooves located between the first end of the wound plug and the breakaway connection,
   wherein in an assembled configuration, the post extends through the rod cavity and is capable of being coupled and decoupled to the breakaway connection such that the first end of the wound plug is positioned adjacent to the second end of the rod, and
   wherein in a deployed configuration, the plurality of annular flanges and the plurality of annular grooves interlock.

2. The apparatus of claim 1, wherein a coupling mechanism of the coupling attachment, and the breakaway connection is one selected from one or more of: a press-fit, a luer lock, a latch, and a cam-lock.

3. The apparatus of claim 1, wherein the coupling attachment of the post is a male component, and the breakaway connection of the wound plug is a female component.

4. The apparatus of claim 1, wherein the post and the rod can be coupled to a second wound plug.

5. The apparatus of claim 1, wherein the second end of the post includes a handle, and the second end of the rod includes an annular plate.

6. The apparatus of claim 1, wherein the proximate portion includes a cavity that extends from the first end of the wound plug to the breakaway connection such that the post extends through the proximate portion of the wound plug in the assembled configuration.

7. The apparatus of claim 1, wherein an outer surface of the proximate portion of the wound plug includes a plurality of barbs.

8. The apparatus of claim 7, wherein the plurality of barbs is unidirectional, and the plurality of barbs includes pointed features pointing towards the second end of the post.

9. The apparatus of claim 7, wherein the plurality of barbs is bidirectional, and the plurality of barbs includes:
   first barbs having first pointed features pointing towards the second end of the post, and
   second barbs having second pointed features pointing towards the first end of the wound plug.

10. The apparatus of claim 1, wherein the first end of the wound plug includes a suprafascial extension, wherein the suprafascial extension is a shape of one or more of: a cup, a stay, and a plate.

11. The apparatus of claim 1, wherein the wound plug further comprises at least one stay coupled to the second end of the wound plug.

12. The apparatus of claim 1, wherein the wound plug excludes a compressible column.

13. The apparatus of claim 1, wherein the apparatus excludes an alignment pin.

14. The apparatus of claim 1, wherein the apparatus excludes a shield.

* * * * *